(12) United States Patent
O'Neill et al.

(10) Patent No.: US 11,096,813 B2
(45) Date of Patent: Aug. 24, 2021

(54) SYSTEM, APPARATUS, AND METHOD FOR CREATING A LUMEN

(71) Applicant: Accumed Radial Systems, LLC, Farmington Hills, MI (US)

(72) Inventors: William W. O'Neill, Grosse Pointe Farms, MI (US); Joseph R. Korotko, Livonia, MI (US)

(73) Assignee: Accumed Radial Systems, LLC, Farmington Hills, MI (US)

( * ) Notice: Subject to any disclaimer, the term of this patent is extended or adjusted under 35 U.S.C. 154(b) by 182 days.

(21) Appl. No.: 15/881,280

(22) Filed: Jan. 26, 2018

(65) Prior Publication Data

US 2018/0147079 A1    May 31, 2018

Related U.S. Application Data

(60) Division of application No. 15/445,234, filed on Feb. 28, 2017, now abandoned, which is a continuation of application No. 14/524,834, filed on Oct. 27, 2014, now abandoned.

(60) Provisional application No. 61/896,052, filed on Oct. 26, 2013, provisional application No. 61/973,510, filed on Apr. 1, 2014.

(51) Int. Cl.
| | | |
|---|---|---|
| *A61F 2/95* | (2013.01) | |
| *A61F 2/958* | (2013.01) | |
| *A61B 17/12* | (2006.01) | |
| *A61B 17/02* | (2006.01) | |
| *A61L 31/16* | (2006.01) | |
| *A61M 25/10* | (2013.01) | |

(52) U.S. Cl.
CPC .......... *A61F 2/958* (2013.01); *A61B 17/0218* (2013.01); *A61B 17/12109* (2013.01); *A61B 17/12136* (2013.01); *A61L 31/16* (2013.01); *A61M 25/104* (2013.01); *A61F 2250/001* (2013.01); *A61F 2250/0067* (2013.01); *A61M 2025/105* (2013.01); *A61M 2025/1093* (2013.01)

(58) Field of Classification Search
CPC ................ A61F 2/958; A61F 2250/001; A61F 2250/0067; A61B 17/0218; A61B 17/12109; A61B 17/12136; A61B 17/320725; A61B 17/3207; A61B 17/320758; A61L 31/16; A61M 25/104; A61M 2025/105; A61M 2025/1093
USPC ......................................................... 606/159
See application file for complete search history.

(56) References Cited

U.S. PATENT DOCUMENTS

| | | | | |
|---|---|---|---|---|
| 5,181,911 A | * | 1/1993 | Shturman | ........... A61M 25/104 604/103.07 |
| 5,370,691 A | * | 12/1994 | Samson | ..................... A61F 2/88 606/194 |
| 6,036,697 A | * | 3/2000 | DiCaprio | ................ A61F 2/958 604/96.01 |

(Continued)

*Primary Examiner* — Erich G Herbermann
(74) *Attorney, Agent, or Firm* — Carlson, Gaskey & Olds, P.C.

(57) ABSTRACT

A method of performing angioplasty includes accessing an artery, inserting a tubular balloon into to the artery in a low-profile operating mode, the tubular balloon constrained in a generally helical shape, and forming a lumen within the generally helical shape by expanding the tubular balloon into a high-profile operating mode. A system for creating a lumen is also disclosed.

16 Claims, 18 Drawing Sheets

(56) References Cited

U.S. PATENT DOCUMENTS

| | | | |
|---|---|---|---|
| 2005/0027345 A1* | 2/2005 | Horan | A61F 2/966 623/1.12 |
| 2005/0049670 A1* | 3/2005 | Jones | A61F 2/91 623/1.12 |
| 2009/0312827 A1* | 12/2009 | Stapleton | A61M 25/104 623/1.11 |
| 2010/0312262 A1* | 12/2010 | Stengel | A61M 25/10184 606/159 |
| 2012/0245520 A1* | 9/2012 | Kelly | A61M 25/1002 604/103.09 |

* cited by examiner

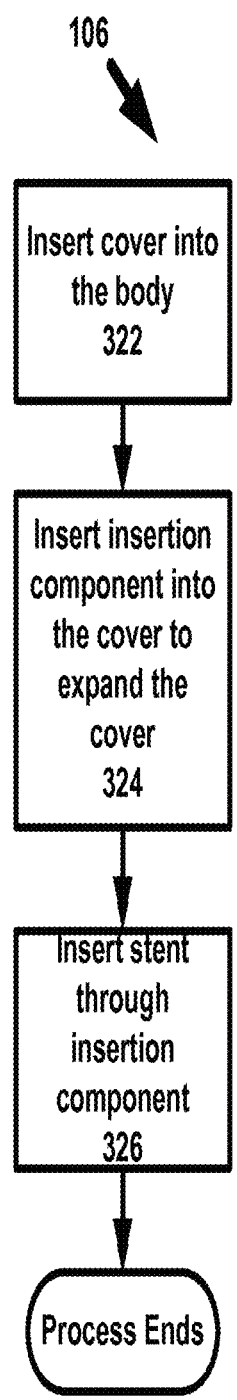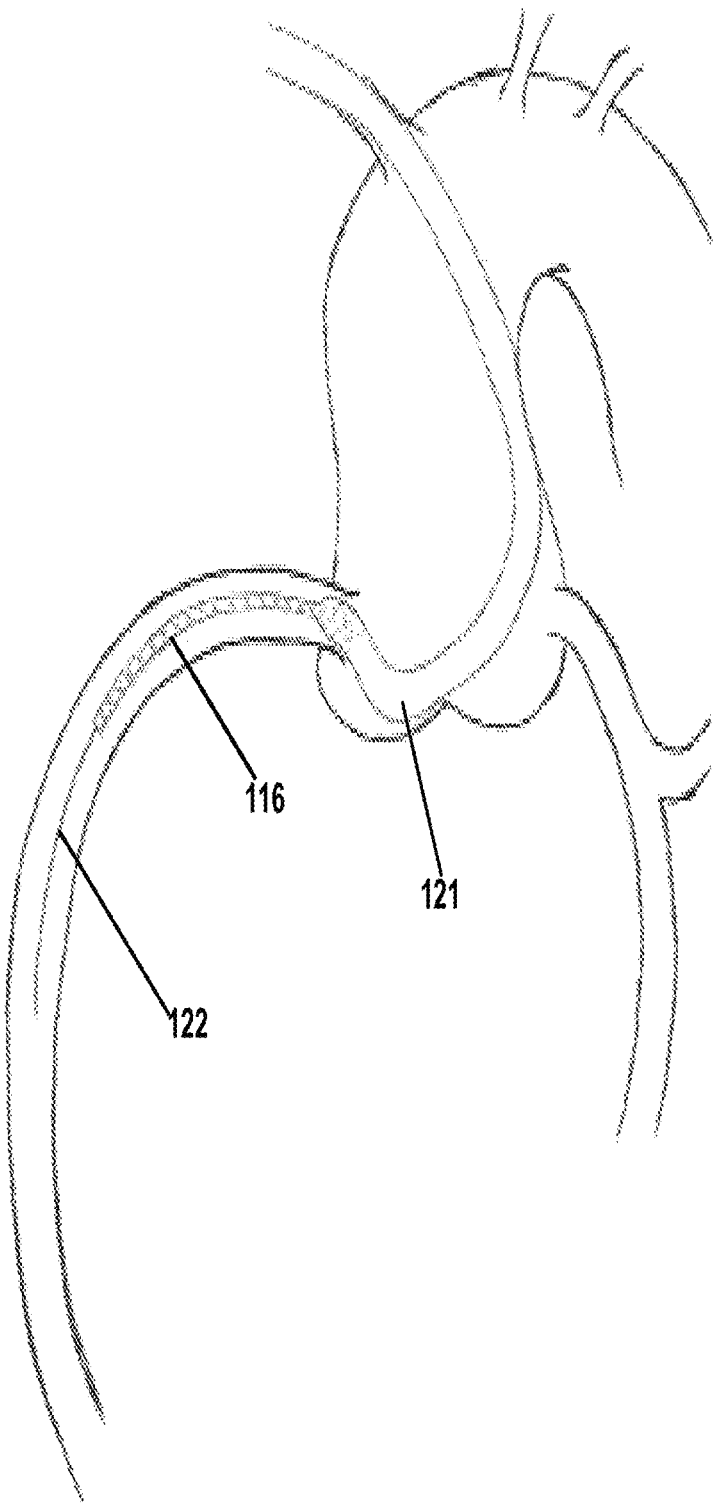
Figure 5a
Figure 5b

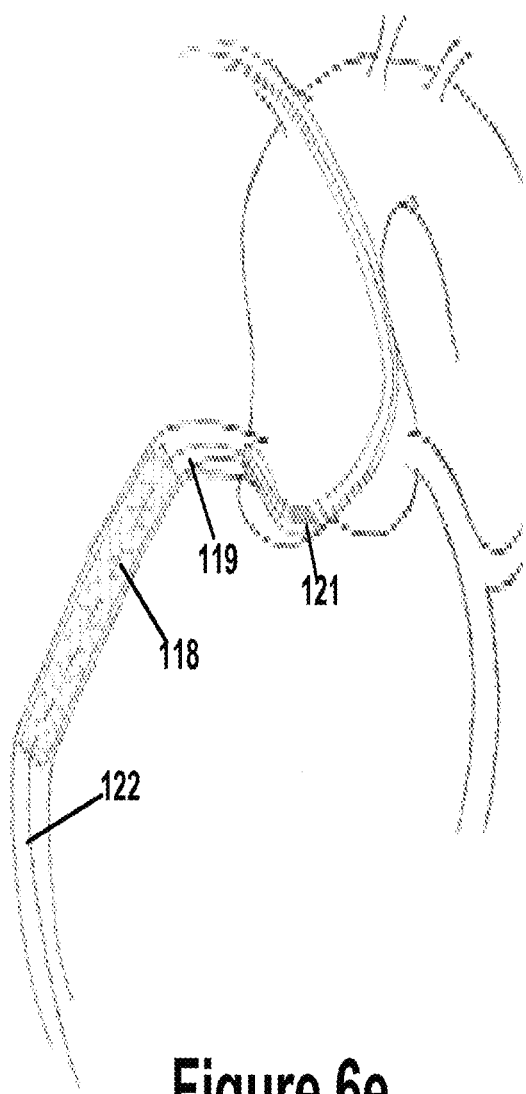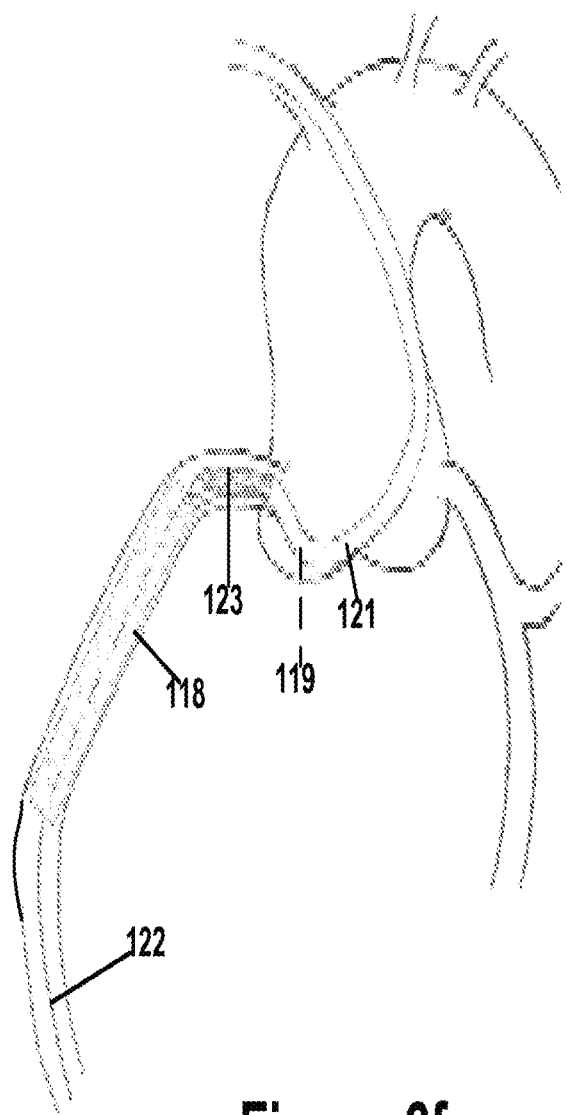
Figure 6e
Figure 6f

SYSTEM, APPARATUS, AND METHOD FOR CREATING A LUMEN

RELATED APPLICATIONS

This application is a divisional of U.S. patent application Ser. No. 15/445,234, filed Feb. 28, 2017, which is hereby incorporated by reference in its entirety and which claims priority to U.S. patent application Ser. No. 14/524,834, filed Oct. 27, 2014, which is hereby incorporated by reference in its entirety, and which claims priority to the following provisional patent applications which are hereby incorporated by reference in their entirety: U.S. Ser. No. 61/896,052 that was filed on Oct. 26, 2013; and U.S. Ser. No. 61/973,510 that was filed on Apr. 1, 2014.

BACKGROUND OF THE INVENTION

The invention is a system, apparatus and method for creating a space (collectively the "system"). More specifically, the system creates a lumen within a body to facilitate the use of a medical device, such as the use of a catheter in a blood vessel. The term "lumen" means a "canal, duct, or cavity of a tubular organ." Although the system can be implemented in a wide variety of different contexts, the original inspiration for the conceptualization of the system arose in the context of catheterization in the blood vessels of human beings. The system can facilitate catheterization by creating additional "working space" (i.e. the lumen) at a desired location within the body of a patient. The additional space can be created by transitioning from a low-profile operating mode into a high-profile operating mode.

I. Catheterization Procedures

The term "catheter" refers collectively to a wide range of medical devices that are inserted into the body to (1) diagnose a medical condition; (2) treat a medical condition; (3) deliver nourishment; or (4) deliver medicine. The term "catheter" is often used more specifically to refer to a tube inserted into the body of a patient for the purposes of (a) removing material from a location in the body of a patient and/or (b) delivering medicinal and/or nourishing material to a specific location within the body of a patient. Catheters can be used in a variety of locations for a variety of purposes within the body of a patient. Catheterization procedures are commonly involved in the diagnosis and treatment of the cardiovascular system, the excretory system, and other similar systems of a patient.

II. Cardiovascular Disease is a Global Threat

The circulation of blood is essential for a healthy body. Blood provides organs and individual cells with oxygen and nutrients necessary to sustain life. Blood also removes cellular metabolic waste products from the body. The proper flow of blood is a prerequisite for good health. At the center of the cardiovascular system is the heart, an organ responsible for pushing blood throughout the body. The heart functions as a pump at the center of a complex network of arteries and veins that make up the cardiovascular system. The cardiovascular system is thus responsible for the delivery of oxygen and nutrients and the removal of certain wastes throughout the body. The performance of the cardiovascular system can be evaluated in terms of cardiac output.

Unfortunately, age, disease, trauma, and/or other ailments can hinder the distribution of blood throughout the body. Cardiovascular diseases are a serious health problem in the United States and elsewhere. About 1 in 3 deaths in the US is attributed to cardiovascular disease, which includes heart attacks and strokes. According to the World Health Organization ("WHO"), cardiovascular diseases are the number one cause of death in world. An estimated 17.3 million people died of cardiovascular diseases in 2008, a number that represents 30% of all deaths occurring in that year. According to WHO estimates, the number of deaths caused by cardiovascular diseases will reach 23.4 million by 2030.

The Centers for Disease Control and Prevention ("CDC") report that "'cardiovascular disease is the leading killer in every racial and ethnic group in America.'" Many health problems in the United States are either rooted in or manifested as cardiovascular disease. The most common type of heart disease in the United States is coronary artery disease ("CAD"). CAD occurs when plaque builds up in the arteries that supply blood to the heart. This can cause the arteries to narrow over time in a process called atherosclerosis. Plaque buildup can also cause chest pain or discomfort resulting from the inadequate supply of blood to the heart muscle. This is commonly referred to as a condition known as angina. Over time CAD can lead to an irregular heartbeat, a condition known as arrhythmia, and even heart failure.

III. Cardiovascular Catheterization Procedures

A variety of catheterization procedures are used in the prior art to diagnose and treat arterial disease. In the context of cardiovascular disease, a catheter is often a long, thin, flexible, hollow intravascular tube used to access the cardiovascular system of the body. Catheterization is most commonly conducted through the radial artery in the wrist (transradial catheterization) or the femoral artery of the groin (transfemoral catheterization). Catheterization can also be conducted through the elbow, neck, and other parts of the body.

A wide variety of intravascular procedures can be used to address cardiovascular health issues in human beings. Percutaneous coronary intervention ("PCI") procedures are a type of intravascular procedure commonly referred to as "coronary angioplasty", "balloon angioplasty" or simply "angioplasty". Patients suffering from atheroscleroisis have narrowed or blocked coronary artery segments resulting from the buildup of cholesterol-laden plaque. Angioplasty is a medical procedure used to treat the narrowed coronary arteries of the heart.

During angioplasty, a cardiologist feeds a deflated balloon or other similar device to the site of the blockage. The balloon can then be inflated at the point of blockage to open the artery. A stent is often permanently placed at the site of blockage to keep the artery open after the balloon is deflated and removed. Angioplasty has proven to be a particularly effective treatment for patients with medically refractory myocardial ischemia. Unfortunately, it is not always possible to position the catheter in the desired location for the purposes of an angioplasty procedure.

IV. Problem of Access

Catheterization procedures can provide a valuable, effective, and minimally invasive option for diagnosing and treating cardiovascular problems and other types of medical problems. Unfortunately, it is not always possible for prior art tools and techniques to reach the blockage site with a catheter. Blockage within a blood vessel can block catheters as well as blood flow. Two common problems of access are vessel tortuosity and insignificant stenoses. The vessel pathway to the blockage that needs treatment may be very tortuous, which means it is very curved or serpentine and the angioplasty balloon catheter cannot be inserted through the tortuous vessel. Also, a portion of the vessel may be stenosed, which means there are smaller blockages that make the vessel too narrow and prevent insertion of the balloon catheter. These smaller blockages are usually not intended to be treated with balloon angioplasty. It would be desirable to empower health care providers with enhanced tools and methodologies for working around obstacles to the blockage site.

SUMMARY OF THE INVENTION

In one example, a method of performing angioplasty includes accessing an artery, inserting a tubular balloon into to the artery in a low-profile operating mode, the tubular balloon constrained in a generally helical shape, and forming a lumen within the generally helical shape by expanding the tubular balloon into a high-profile operating mode.

In one example, a system for forming a lumen includes a tubular balloon operable in a low-profile operating mode and a high-profile operating mode, and a matrix constraining the tubular balloon in a generally helical shape, the matrix comprising a weave. The tubular balloon has a first diameter in a low-profile operating mode and a second diameter in a high-profile operating mode, and the second diameter is larger than the first diameter.

In another one example, a system for forming a lumen includes a tubular balloon, the tubular balloon operable in a low-profile operating mode and a high-profile operating mode, and a matrix constraining the tubular balloon in a generally helical shape, the matrix comprising at least one thermally formed connection. The tubular balloon has a first diameter in a low-profile operating mode and a second diameter in a high-profile operating mode, and the second diameter is larger than the first diameter.

BRIEF DESCRIPTION OF THE DRAWINGS

Many features and inventive aspects of the system, are illustrated in the following drawings. However, no patent application can disclose all of the potential embodiments of an invention. In accordance with the provisions of the patent statutes, the principles and modes of operation of the system are explained and illustrated in certain preferred embodiments. However, it must be understood that the system may be practiced otherwise than is specifically explained and illustrated without departing from its spirit or scope.

The description of the system and the various illustrations of the system should be understood to include all novel and non-obvious combination of elements described herein, and claims may be presented in this or a later application to any novel and non-obvious combination of these elements. Moreover, the foregoing embodiments are illustrative, and no single feature or element is essential to all possible combinations that may be claimed in this or a later application.

FIG. 5a is a flow chart diagram illustrating an example of a process for creating a lumen using an insertion component embodiment of the system.

FIG. 5b is an environmental diagram illustrating an example of a process step where the cover is inserted into the body of the patient.

FIG. 6*e* is an environmental diagram illustrating an example of how the expanded sheathed balloon can create or enhance the lumen at the desired location within the body of the patient.

FIG. 6*f* is an environmental diagram illustrating an example of a process step where the stent catheter is inserted into the patient through the working space created by the presence of the balloon in a high-profile operating mode.

DETAILED DESCRIPTION

Figure 1A:
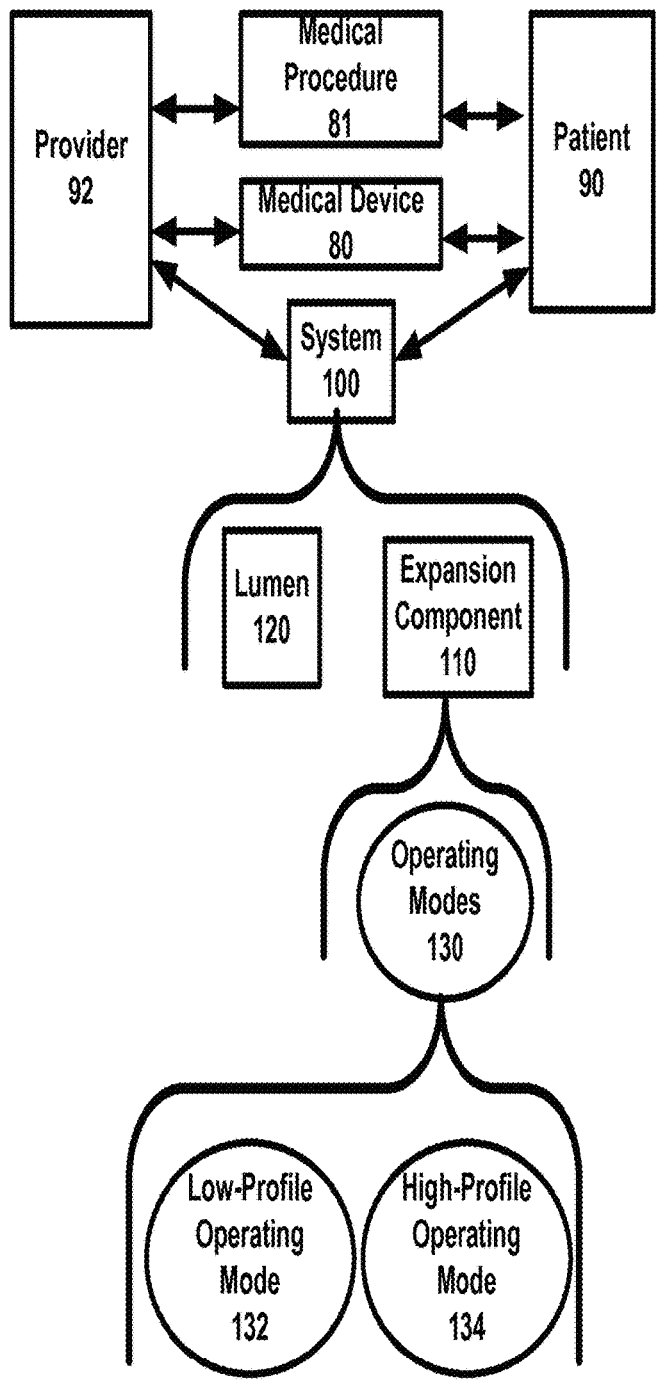
FIG. 1a is a block diagram illustrating an example of a system for creating a lumen.

The invention is a system, apparatus and method for creating a space (collectively the "system"). More specifically, the system creates a lumen within a body to facilitate the use of a medical device, such as the use of a catheter in a blood vessel. The term "lumen" means a "canal, duct, or cavity of a tubular organ." Although the system can be implemented in a wide variety of different contexts, the original inspiration for the conceptualization of the system arose in the context of catheterization in the blood vessels of human beings. The system can facilitate catheterization by creating additional "working space" (i.e. the lumen) at a desired location within the body of a patient. The additional space can be created by transitioning from a low-profile operating mode into a high-profile operating mode. The additional space can enable the use of other medical devices by overcoming the problems of conventional access such as vessel tortuosity or insignificant stenoses. The system enables a balloon angioplasty catheter or stent catheter can be inserted through the passageway or tunnel of the lumen past the access problems and onto the desired location.

All of the numbered elements illustrated in the drawings and discussed in the text below that pertain to structural components rather than process steps are defined in the glossary provided in Table 1 below.

I. Overview

The system can create a lumen in the body of a patient. That lumen can be used to position a medical device, such as a catheter, that can potentially save the life of the patient. The system can be described in terms of interacting entities, components, operational attributes, and processes.

A. Entities

As illustrated in FIG. 1*a*, a system 100 is an interface between a healthcare provider 92 and a body of a living organism, i.e. a patient 90. The provider 92 is typically a physician, although nurses, paramedics, physician assistants, veterinarians, and other health care professionals can potentially act as providers 92 in certain contexts. The patient 90 is typically a human being, but other organisms can constitute patients 90 in certain contexts. The system 100 is a tool that the provider 92 can use to benefit the health status of the patient 90.

B. System

The purpose of the system 100 is to create "working space" (i.e. a lumen 120) within the body of the patient 90 sufficient to enable the positioning and use of a medical device 80 such as a catheter within the body of the patient 90. The system 100 can be implemented in a wide variety of different ways. The system 100 can be used to improve the health of the patient 90 and to even save the life of the patient 90.

C. Medical Devices and Medical Procedures

A wide variety of different medical devices 80 and medical procedures 81 can benefit from the lumen 120 created by the system 100. Examples of potentially useful medical devices 80 include but are not limited to all types of catheters, stents, patient monitoring applications, and other similar invasive devices.

A catheter device is potentially any device inserted into the body of a patient 90. The term "catheter device" refers collectively to a wide range of medical devices that are inserted into the body to (1) diagnose a medical condition; (2) treat a medical condition; (3) delivery nourishment; or (4) deliver medicine. The term "catheter device" is often used more specifically to refer to a tube inserted into the body of a patient 90 for the purposes of (a) removing material from a location in the body of a patient 90 and/or (b) delivering medicinal and/or nourishing material to a specific location within the body of a patient 90. Catheters can be used in a variety of locations for a variety of purposes within the body of the patient 90. Catheterization procedures are commonly involved in the diagnosis and treatment of the cardiovascular system, the excretory system, and other systems of a patient 90.

The system 100 was originally conceived for the purpose of serving providers 92 involved in providing medical procedures 81 such as coronary vascular procedures. Examples of such procedures include but are not limited to Percutaneous Coronary Intervention (PCI), Percutaneous Coronary Angiogram (PCA), Chronic Total Occlusions (CTO), Stent implantation, Atherectomy, and Embolic Protection. The system 100 can be particularly useful in the context of transradial catheterizations (catheterizations in which the catheter initially enters the body of the patient 90 through the radial artery) because transradial catheterizations typically involve catheterization devices with a relatively smaller profile and relatively sparse space in which to operate. The system 100 in its varying embodiments can also be used in a variety of contexts that involve cardiovascular care and the treatment of wholly different conditions.

D. Lumen

A lumen 120 is a space created within the patient 90 by the system 100. The lumen 120 is often referred to as a "canal, duct, or cavity within a tubular organ". The lumen 120 is the "working space" within the patient 90 in which the medical device 80 is positioned. In many embodiments of the system 100, the lumen 120 is located within the expansion component 110 and the expansion component 110 is at least substantially in the form a hollow tube, with the lumen 120 comprising the hollow core of the expansion component 110.

E. Expansion Component

An expansion component 110 is the device capable of existing in at least two operating modes 130, a low-profile operating mode 132 and a high-profile operating mode 134.

There are a wide variety of different embodiments of expansion components 110 that can be incorporated into a wide variety of different embodiments of the system 100. In many embodiments of the system 100, the expansion component 110 can transform from a high-profile operating mode 134 back into a low-profile operating mode 132 when the expansion component 110 is no longer needed. In many embodiments, it will be easier for the provider 92 to remove the expansion component 110 from the patient 90 when the expansion component 110 is in a low-profile operating mode 132.

Expansion components 110 can be categorized as direct vs. indirect. Some embodiments of the system 100 utilize balloons as expansion components 110 while other embodiments of the system 100 utilize non-balloon expansion components 110.

F. Operating Modes/States

The expansion component 110 can operate in two or more operating modes 130 (which can also be referred to as states 130. The low-profile operating mode 132 is typically the most convenient operating mode 130 in which to insert the expansion component 110 into the patient 90 prior to creating the lumen 120. The low-profile operating mode 132 is also typically the most convenient operating mode 130 in which the provider 92 can remove the expansion component 110 after the lumen 120 is created and after the medical device 80 has been positioned correctly within the patient 90.

Some embodiments of the system 100 will involve one or more intermediate operating modes between the low-profile operating mode 132 and the high-profile operating mode 134.

G. Process Flow View

Figure 1B:
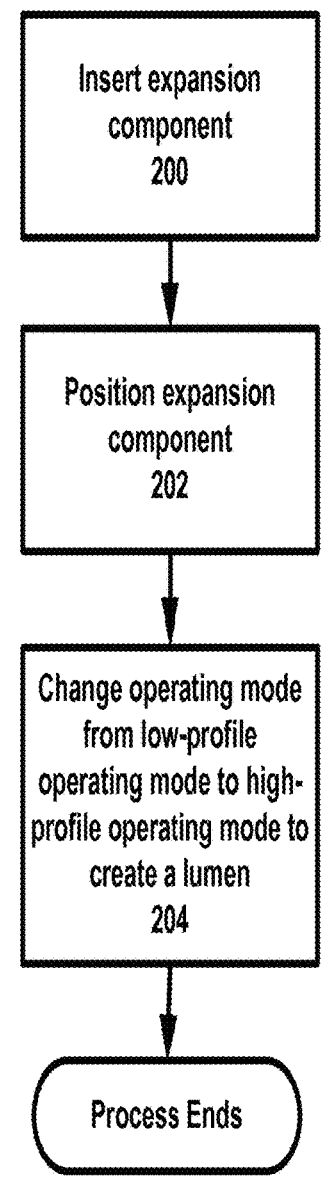
FIG. 1b is a flow chart diagram illustrating an example of a process for creating a lumen.

The system 100 can be described as a series of process steps as well as a configuration of interacting elements. FIG. 1b is a flow chart diagram illustrating an example of a method for creating a lumen 120.

At 200, the expansion component 110 is inserted within the patient 90. Different embodiments of the system 100 can involve different types of expansion components 110 to create lumen 120 for different types of medical devices 80.

At 202, the expansion component 110 is positioned within the patient 90. Different embodiments of the system 100 can involve a wide variety of different locations within the body of the patient 90.

At 204, the operating mode 130 of the expansion component 110 is changed from a low-profile operating mode 132 into a high-profile operating mode 134 in order to create a lumen 120. It is the lumen 120 that serves as the "working space" for the proper positioning and use of the medical device 80, such as a catheter.

In many embodiments, after the lumen 120 is created and medical device 80 is properly positioned, the expansion component 110 is transformed back from a high-profile operating mode 134 into a low-profile operating mode 132 to facilitate the removal of the expansion component 110 from the body of the patient 90.

H. Operating Environment

The system 100 can be implemented in a wide variety of different operating environments and locations. The process of determining which embodiment of the system 100 is best suited for a particular context should begin with identifying the desired medical device 80 to be used at the desired location. The appropriate expansion component 110 can then be identified and selected.

Figure 1C:
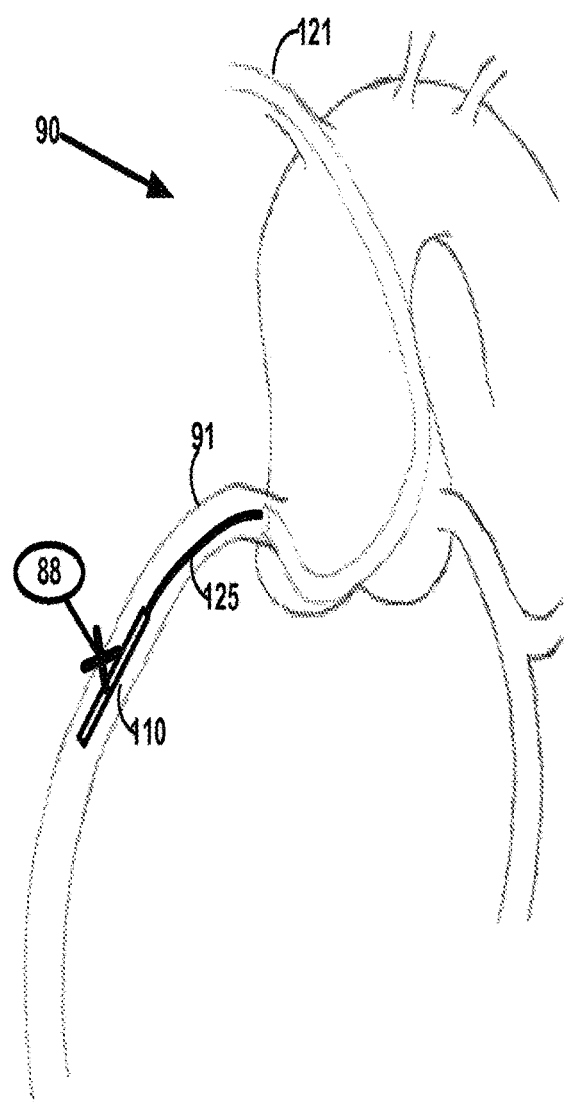
FIG. 1c is an environmental diagram illustrating an example of an expansion component in a low-profile operating mode.

FIG. 1c is an environmental diagram illustrating an example of an expansion component 110 in a low-profile operating mode 132. The expansion component 110 is being positioned to a desired location 88 within a blood vessel 91 in the patient 90.

Figure 1D:
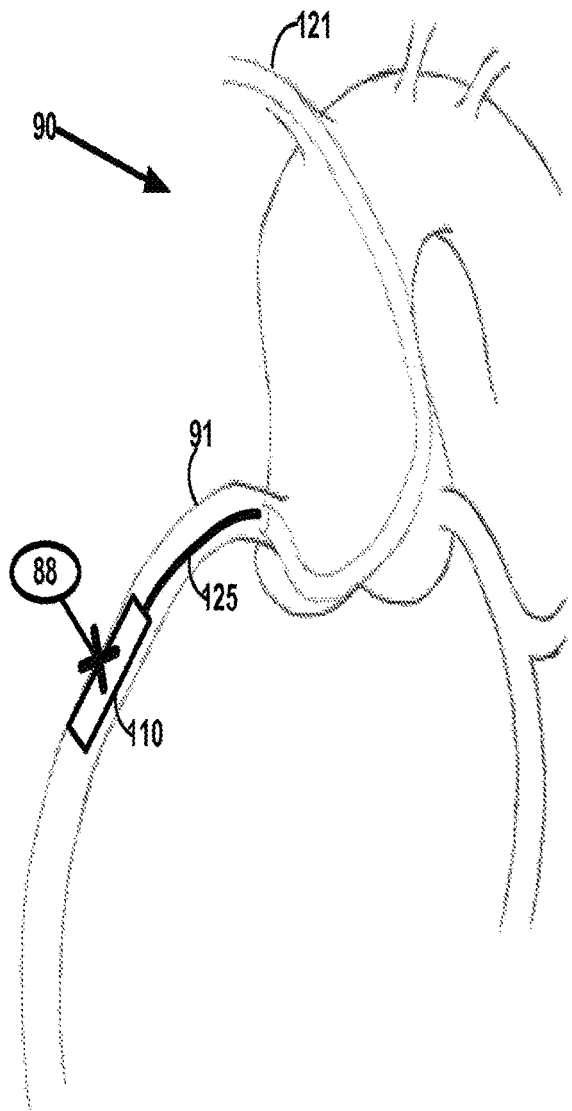
FIG. 1d is an environmental diagram illustrating an example of an expansion component in a high-profile operating mode.

FIG. 1d is an environmental diagram illustrating an example of an expansion component 110 that has been transformed (i.e. expanded) from a low-profile operating mode 132 into a high-profile operating mode 134.

I. Ancillary Components

In many embodiments of the system 100, the expansion component 110 is but one component of many. For example, in the illustrations of FIGS. 1c and 1d the expansion component 110 can interfaces with certain ancillary components, such as a guide catheter 121 and a guide wire 122. In navigating the various narrow blood vessels 91 a variety of guide catheters 121 and guide wires 122 may be utilized to position the expansion component 110 to the desired location 88. Such components may be part of the system 100, but the use of ancillary components will vary widely between different embodiments of the system 100. The system 100 can include virtually any prior art component useful to the provider 92 in addressing the needs of the patient 90.

II. Alternative Embodiments

Many features and inventive aspects of the system 100 are illustrated in the figures and described in the text of this application. However, no patent application can disclose all of the potential embodiments of an invention. In accordance with the provisions of the patent statutes, the principles and modes of operation of the system 100 are explained and illustrated in certain preferred embodiments. However, it must be understood that the system 100 may be practiced otherwise than is specifically explained and illustrated without departing from its spirit or scope.

The description of the system 100 and the various illustrations of the system 100 should be understood to include all novel and non-obvious combination of elements described herein, and claims may be presented in this or a later application to any novel and non-obvious combination of these elements. Moreover, the foregoing embodiments are illustrative, and no single feature or element is essential to all possible combinations that may be claimed in this or a later application.

There are various categories that can be useful in describing various embodiments of the system 100.

A. Direct Vs. Indirect

With respect to all embodiments of the system 100, the expansion component 110 expands from a low-profile operating mode 132 into a high-profile operating mode 134 to create a lumen 120. For some embodiments of the expansion component 110, the transformation between operating modes 130 is accomplished directly by the expansion component 110 while in other embodiments of the expansion component 110, the transformation between operating modes is accomplished only indirectly by the expansion component 110.

Figure 2A:
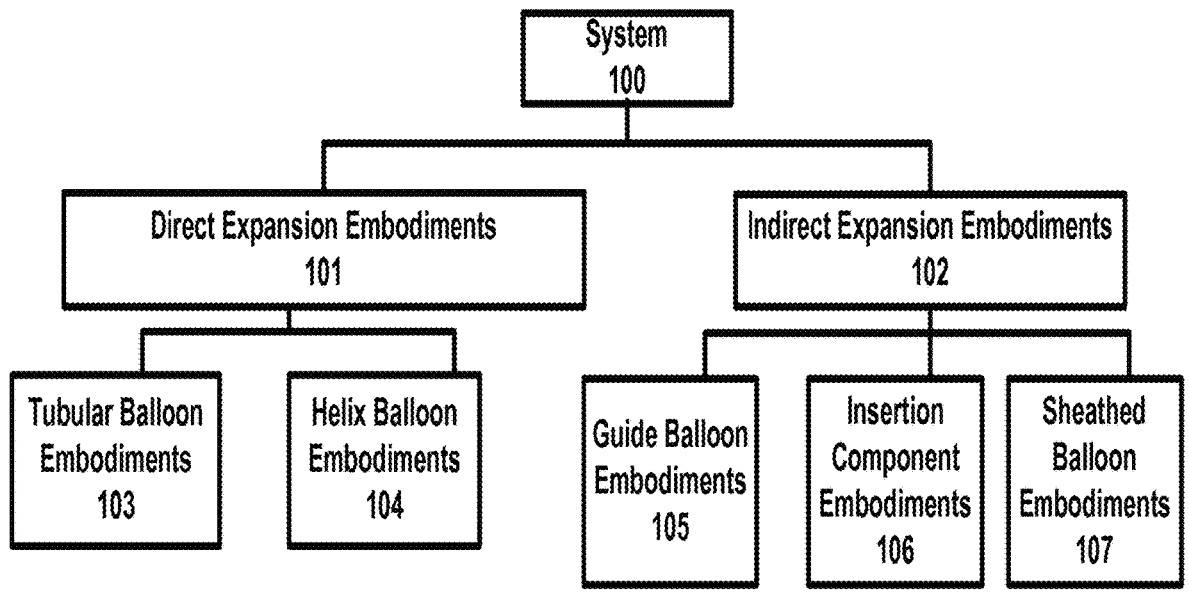
FIG. 2a is a hierarchy diagram illustrating an example of different embodiments of the system, including direct expansion embodiments and indirect expansion embodiments of the system.

FIG. 2a is a hierarchy diagram illustrating examples of direct expansion embodiments 101 as well as indirect expansion embodiments 102. Indirect expansion embodiments 102 involve expansion components 110 that expand or shrink due to other components of the system 100. In contrast, direct expansion components 101 involve expansion components 110 that can change operating modes 130 without the use of other components of the system 100.

Direct expansion embodiments 101 can include but are not limited to a tubular balloon embodiment 103 and a helix balloon embodiment 104. Direct expansion embodiments 101 typically involve "inflating" a balloon with a substance such as liquid to expand from a low-profile operating mode 132 into a high-profile operating mode 134. Some embodiments may utilize a gas, but it is often not desirable to risk inserting bubbles of air or other gases in the blood vessels 91 of patients 90.

Indirect expansion embodiments 102 can include but are not limited to a guide balloon embodiment 105 (where an expansion component 110 in the form of a cover 116 expands by advancing upon an inflated guide balloon 115), an insertion component embodiment 106 (where an expansion component 110 in the form of a cover 116 expands through the insertion of an insertion component 117 into the expansion component 110), and a sheath embodiment 107 (where the sheathed balloon 118 inflates when no longer constrained by the sheath 119). Indirect expansion embodiments 102 utilize other components of the system 100 to "inflate" to a high-profile operating mode 134 and to "deflate" to a low-profile operating mode 132. Guide balloon embodiments 105 of the system 100 use an expansion component 110 that is advanced over an inflated balloon to expand the expansion component 110. Insertion component embodiments 106 of the system 100 use a insertion component 117 that is inserted into the expansion component 110 to expand the expansion component 110. Sheath embodiments 107 utilize a sheath to constrain an expansion component 110 that would otherwise exist in an expanded state.

B. Expansion Component Balloons Vs. Non-Balloons

Just as different embodiments of the system 100 can be categorized on whether the expansion component 110 is directly or indirectly expanded, the various embodiments of the system 100 can also be categorized on the basis of whether the expansion component 110 is some type of balloon (which inflates using air, some other gas, some form of liquid or fluid, or through the use of mechanical means) or whether the expansion component 110 is not a balloon.

Figure 2B:
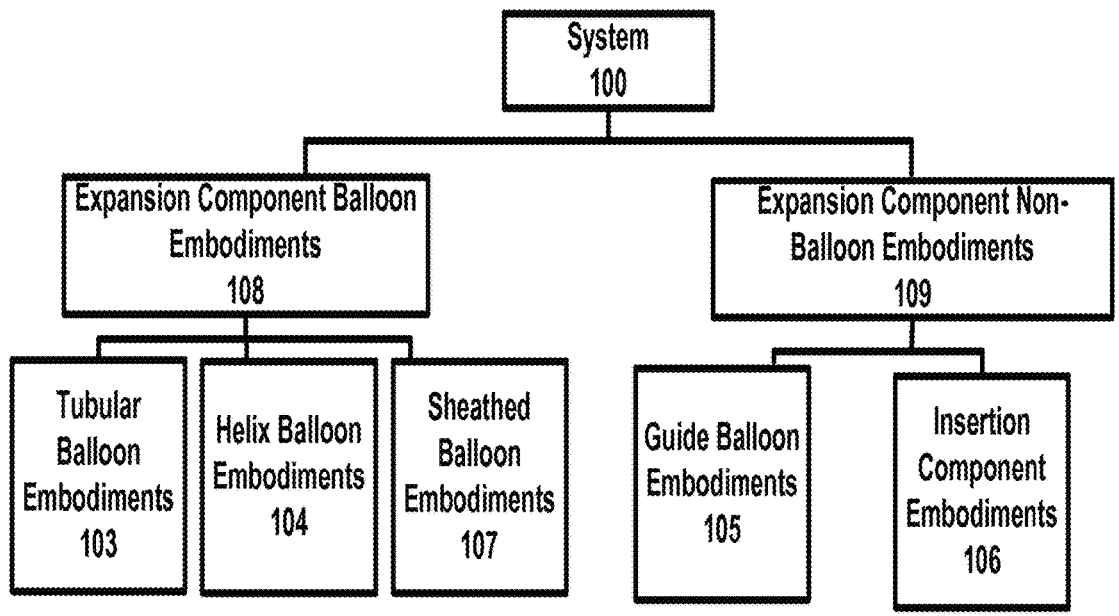
FIG. 2b is a hierarchy diagram illustrating an example of different embodiments of the system, including expansion component balloon embodiments and expansion component non-balloon embodiments.

FIG. 2b is a hierarchy diagram illustrating examples of both expansion component balloon embodiments 108 and expansion component non-balloon embodiments 109.

Examples of expansion component balloon embodiments 108 can include but are not limited to tubular balloon embodiments 103, helix balloon embodiments 104, and sheath embodiments 107.

Examples of expansion component non-balloon embodiments 109 can include but are not limited to guide balloon embodiments 105 and insertion component embodiments 106.

C. Active Vs. Passive Expansion Components

Many differences in various embodiments of the system 100 are dictated by the differences in the expansion components 110 of the different embodiments. Two overarching categories of expansion components 110 can be differentiated on the basis of whether they are "active" or "passive".

1. Active Expansion Components/Active Apparatuses
  a. Balloon Without Sheath

The embodiment of the system 100 illustrated in FIGS. 3a-3g involves an inflatable balloon as the expansion component 110. That embodiment of the system 100 has a balloon as the expansion component 110 that can be in either a low-profile state 132 or a high-profile state 134 (i.e. an expanded state). The system 100 is transitioned between states 130 by inflating or deflating the expansion component 110 (i.e. the balloon). The system 100 has an "active" control through the inflation and deflation feature.

b. Balloon With Sheath

An alternate embodiment of an active control system 100 is a self-expanding balloon with a sheathed balloon 118 as the expansion component 110. The system 100 would have a balloon that self-expands. Active control of the system 100 is through the use of a sheath 119 that covers the balloon. The device is in the low-profile state 132 when the sheath 119 covers the self-expanding balloon. In this state 132 the system 100 can be inserted to the required location. The low-profile state 132 will facilitate insertion in an atraumatic manner. In this state 132, the system 100 will be able to interface with other necessary devices, such as a 0.014 coronary guide wire and a guide catheter. When the system 100 is properly positioned at the required location, the sheath 119 is retracted by active control which allows the expansion component 110 to self-expand to the expanded high-profile state 134. In the expanded high-profile state 134 the system 100 can enable the performance of medical procedures 81 involving the insertion of other medical devices 80 such as a catheter device. It will provide a space 120 through which other devices can be inserted. When the expanded state 134 is not required anymore, the sheath 119 can be advanced over the balloon 118 with active control and transition the system 100 back to the low-profile state 132.

Another potential alternative means to achieve a self-expanding expansion component 110 is to use materials with a spring feature. Many metals have a spring feature, such as stainless steels. Alternately, shape memory metals such as Nitinol could be used to achieve a self-expanding feature. It is envisioned that there may be other materials, either metals or non-metals, which could be used to achieve a self-expanding feature. These materials can be used to make a structure that serves as a "sheathed balloon" 118. In some embodiments, the sheathed balloon 118 can be similar to other types of balloons 111. In other embodiments, the sheathed balloon 118 can be a self-expanding braid structure 124.

2. Passive Expansion Components/Passive Apparatuses

A passive control system is a system 100 that has two or more operating modes 130, and the system 100 is passively transitioned between the states 130 instead of actively transitioned between states 130.

a. Pleated Expansion Component

Figure 3A:
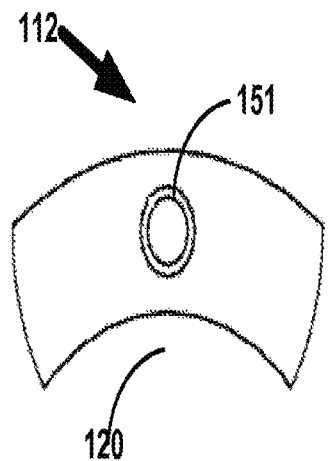
FIG. 3a is diagram illustrating a partial and close-up view of the tubular balloon expansion component illustrated in FIG. 3b.
Figure 3B:
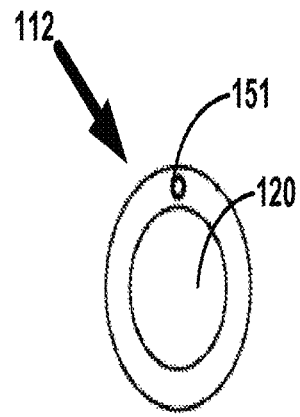
FIG. 3b is a diagram illustrating an example of an axial view of the tubular balloon expansion component.
Figure 3C:
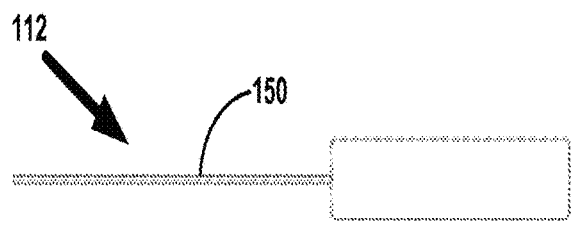
FIG. 3c is a diagram illustrating an example of a top view of the tubular balloon expansion component.
Figure 3D:
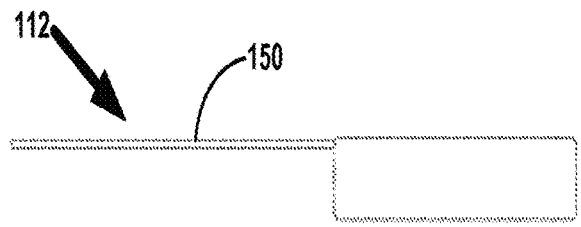
FIG. 3d is a diagram illustrating an example of a side view of the tubular balloon expansion component.
Figure 3E:
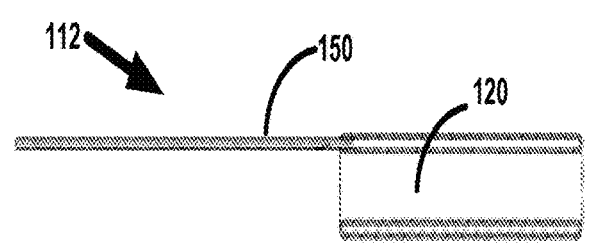
FIG. 3e is a diagram illustrating an example of a cross-sectional view of a side view of the tubular balloon expansion component with an illustration of a space within the tubular balloon expansion component.
Figure 3F:
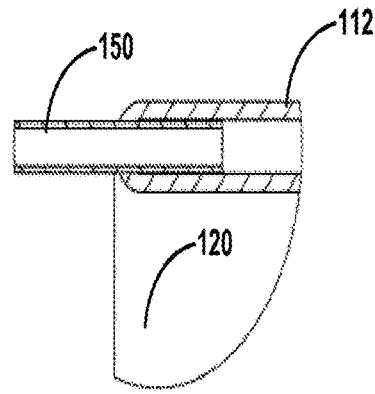
FIG. 3f is a diagram illustrating an example of a partial and close-up view of the tubular balloon expansion component illustrated in FIG. 3e.
Figure 3G:
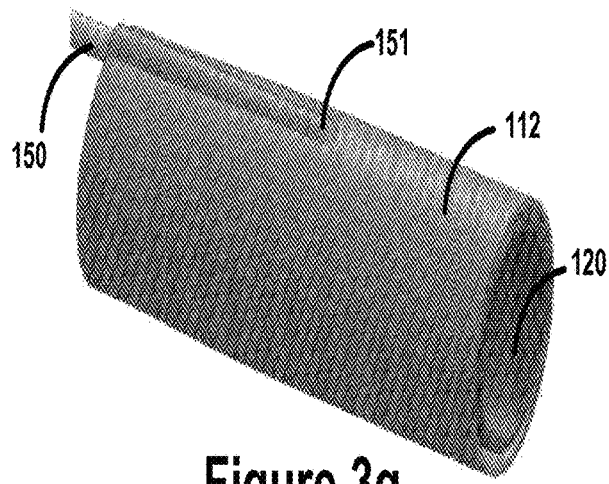
FIG. 3g is a perspective and partial diagram illustrating an example of a tubular balloon expansion component.
Figure 3H:
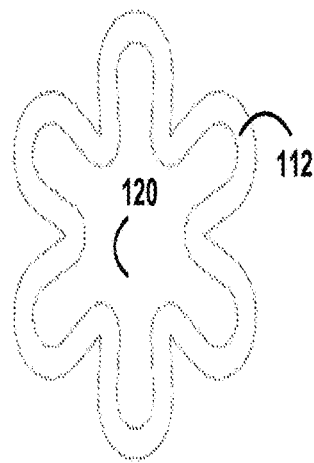
FIG. 3h is a diagram illustrating an example of a front view of a pleated tubular expansion component, an example of a passive expansion component.
Figure 3I:
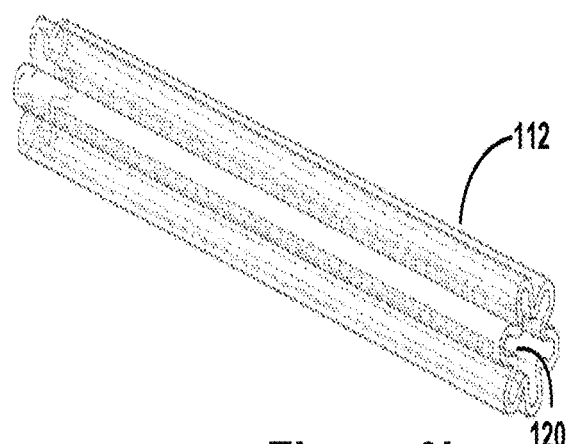
FIG. 3i is a diagram illustrating an example of a perspective view of tubular balloon expansion component

One embodiment of a passive control is a pleated expansion component 110 as illustrated in FIGS. 3h and 3i. The expansion component 110 of the system 100 would be made with pleats. The pleats cause the expansion component 110 to have a low-profile state 132. The expansion component 110 is small because of its pleated shape. When a different medical device 80 is inserted into the space 120, or pleated expansion component 110, it will passively expand to the larger expanded state 134 to allow the other medical device 80 to pass through. The other medical device 80 will force the pleats to expand outward to form a larger space 120 and a more expanded expansion component 110. For this embodiment, the system 100 is passively transitioned between the two states 130 by the insertion of the assisted device, not the active operation of the system 100 by the operator.

b. Elastic Expansion Component

An alternate embodiment of a passive control system 100 is an elastic expansion component 110. The elastic expansion component 110 would be made of elastic or stretchable materials. The expansion component 110 would be made in the low-profile state 132. Its cross section is likely to be a round shape, but other shapes are possible, such as elliptical. When a different medical device 80 is inserted into to the elastic expansion component 110 it will passively expand to a larger state to allow the other medical device to pass through. The other medical device 80 will force the elastic expanding component 110 to form a larger space 120. For such an embodiment, the system 100 is passively transitioned between the two states 130 instead of actively transitioned by the operator. A system 100 of this design could be made from a variety of materials, such as medical grade silicones or urethanes.

D. Embodiment Categories

Figure 2C:
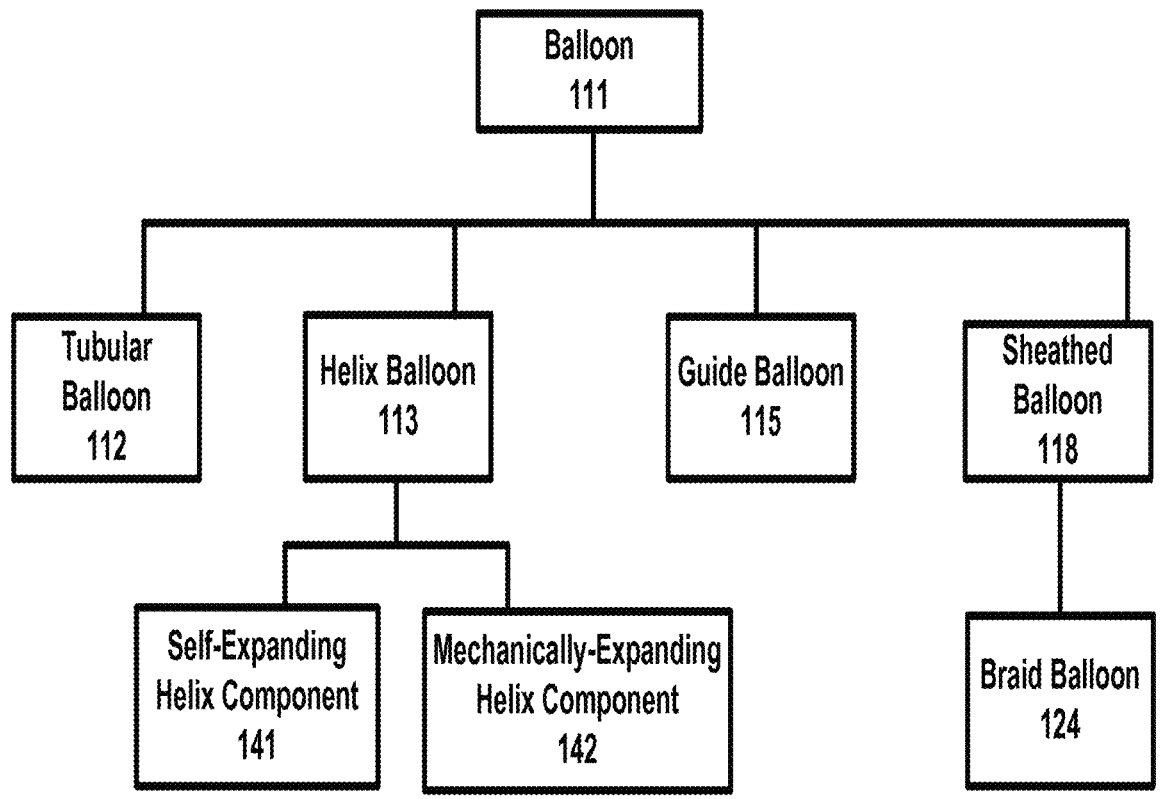
FIG. 2c is a hierarchy diagram illustrating an example of different types of balloons that can be utilized by the system.

As illustrated in both FIG. 2a and FIG. 2b, the various embodiments of the system 100 can be organized into categories. As illustrated in FIG. 2c, many different embodiments of the system 100 can utilize some form of a balloon 111. Some embodiments of the system 100 can utilize a balloon 111 with a default state of uninflated that require inflation to transition from a low-profile operating mode 132 into a high-profile operating mode 134 (i.e. the tubular balloon 112 and the helix balloon 113). Other embodiments of the system 100 use the balloon 111 not as the expansion component but as a mechanism for expanding the expansion component 110 from a low-profile operating mode 132 into a high-profile operating mode 134 (i.e. the guide balloon 115 on which a cover 116 is advanced). Still other embodiments utilize a balloon 111 that has a default state of inflated or that self-inflates (i.e. a sheathed balloon 118). A sheathed balloon 118 transitions from a low-profile operating mode 132 into a high-profile operating mode 134 when it is removed from the constraining sheath 119. The sheathed balloon 118 can be returned to the low-profile operating mode 132 by being positioned back within the sheath 119.

The system 100 can be implemented using expansion components 110 that are (1) integrated into a single stand-alone device with other components of the system 100; (2) a non-integrated collection of components configured to function with certain supporting components; (3) a magnitude of integration that falls between these two polar opposites.

As indicated by the various arrows in FIG. 1a, the system 100 can directly interact with both the patients 90 and providers 92. Such a system 100 can be implemented in a wide variety of different alternative embodiments. Some embodiments of the system 100 can be single stand-alone components, such as an expandable balloon 111. Other embodiments of the system 100 can involve configurations of multiple components which may be permanently attached to each other, or merely configured to temporarily act in concert with each other.

The system 100 can be used in conjunction with virtually any catheter device 80 and as part of virtually any catheterization procedure. It facilitates a catheterization procedure by aiding the insertion of medical devices 80 such as various catheters and potentially other devices to the desired location 80 in the body of the patient 90 that cannot otherwise be reached without the space 120 created by the system 100 transitioning from a low-profile operating environment 132 into a high-profile operating environment 134.

By way of example, an angioplasty balloon catheter or a stent catheter may not otherwise able to be placed in the desired location 88 where the blockage is located. The system 100 can facilitate inserting the balloon or stent 123 (i.e. the catheter device) to the blockage.

The advantage of the system 100 is that it can be inserted to required locations by itself that medical devices 80 such as catheters cannot be inserted by themselves. The ability to exist in either of two states 130 enables the system 100 to have this advantage. Unlike medical devices 80 such as catheterization devices that expand to remove blockage in an artery, the system 100 can be configured for the purpose of merely expanding sufficiently to create operating space for the catheter device. The operating space 120 is in the form of a lumen or passageway created by the expanded state of the system 100. Other catheterization devices can pass through the operating space 120 in order to be inserted to their desired location 88. The operating space 120 can create safe passage for catheterization devices 88 through tortuous (serpentine) vessels 91 or past stenoses that impinge vessels 91. The system 100 may temporarily straighten out tortuous vessels or dilate stenosed areas.

The system 100 works in a supportive role with respect to a medical device 80, such as catheter. In the context of cardiovascular catheterization, the system 100 is typically inserted into coronary arteries, or other arteries or veins (collectively "vessels" 91). The system 100 can be appropriately sized and constructed to accomplish the desired task of creating an additional space 120 for the desired catheter device at the desired location 88. The system 100 can have two or more states 130, with a low-profile state 132 for insertion and removal of the device, and an expanded state 134 for coronary stabilization.

The original context inspiring the conception of the system 100 was to facilitate percutaneous coronary intervention (PCI) procedures, or other similar intravascular procedures. However, the system 100 can be configured for use with virtually any catheter device and any catheterization procedure.

The system 100 can be made from biocompatible medical grade materials, such as polymers (plastics) and metals. The system 100 may be made from materials or have coatings that give it additional features. It may have a hydrophilic feature. It can be made using various manufacturing methods, such as extrusion, injection molding, thermal forming, thermal bonding, wire forming methods, laser manufacturing methods or other manufacturing methods. It will be made in such a way that it can be properly packaged and sterilized. Likely sterilization methods would be e-beam radiation, gamma radiation, ethylene oxide (EO) gas sterilization or nitrous oxide (NO2) gas sterilization.

1. Tubular Balloon Embodiments

In a tubular balloon embodiment 103 of the system 100, the expansion component 110 is a tubular balloon 112. FIGS. 3a-3i pertain to tubular balloon embodiments 103 of the system 100.

The tubular balloon 112 can be inflated with air, other forms of gas, water, and other forms of liquids or fluids. In some tubular balloon embodiments 103, the tubular balloon 112 can be inflated with mechanical means such as a spring that is uncompressed or other similar means.

2. Helix Balloon Embodiments

In a helix balloon embodiment 104 of the system 100, the expansion component 110 is a helix balloon 113, i.e. a tubular balloon 112 that is constrained by a matrix 114 to form an at least substantially helical shape. FIGS. 7a-7e illustrate examples of helix balloon embodiments 104.

Just as with tubular balloon embodiments 103, helix balloon embodiments 104 can utilize a wide variety of different inflating mechanisms.

Helix balloon embodiments 104 can be highly desirable because of the impact of the matrix 114, which can selectively increase the rigidity of the expansion component 110 so that it can be inserted into locations 88 that a tubular balloon 112 without a matrix 114 will not be able to reach. As illustrated in FIG. 2c, helix balloons 113 can be implemented as conventional inflatable balloons, but also as a self-expanding helix component 141 or as a mechanically-expanding helix component 142.

3. Sheath Embodiments

A sheath embodiment 107 of the system 100 uses a balloon 111 that does not require inflation to transition from a low-profile operating mode 132 into a high-profile operating mode 134. FIGS. 6a-6g pertain to sheath embodiments 107 of the system 100. A sheathed balloon 118 transitions from a low-profile operating mode 132 into a high-profile operating mode 134 when it is removed from the constraining sheath 119. The sheathed balloon 118 can be returned to the low-profile operating mode 132 by being positioned back within the sheath 119.

As illustrated in FIG. 2c, a sheathed balloon 118 can be implemented as a braid balloon 124.

4. Guide Balloon Embodiments

A guide balloon embodiment 105 of the system 100 involves an expansion component 110 that is not a balloon 111. Rather, the expansion component 110 is a cover 116 that is advanced over a preceding inflated balloon, i.e. a guide balloon 115. FIGS. 4a-4g illustrated examples of guide balloon embodiments 105 of the system 100.

5. Insertion Component Embodiments

Insertion component embodiments 106 of the system 100 need not use any kind of balloon 111 in the expansion/shrinkage processes. In an insertion component embodiment 106 of the system 100, an insertion component 117 is inserted into the expansion component 110 to cause the expansion component 110 to expand from a low-profile operating mode 132 into a high-profile operating mode 134. The expansion component 110 in an insertion component embodiment 106 of the system 100 can be a cover 116, such as another catheter. Insertion component embodiments 106 are illustrated in FIGS. 5a-5d.

III. Tubular Balloon Embodiments

Some embodiments of the system 100 will utilize a single tubular balloon 112 to serve as the expansion component 110 to facilitate the transition between a low-profile state 132 and a high-profile state 134 that can create a lumen 120 for the applicable medical device 80, such as a balloon angioplasty catheter or stent 123, at the desired location 88 in the body of the patient 90.

The "working space" or lumen 120 created by the expansion of a tubular balloon 112 into a high-profile operating mode 134 is created within the tubular balloon 112. Examples of different types of expansion components 110 can include inflatable balloons 112 with a "donut hole" space (see FIGS. 3a-3i), As discussed above, some embodiments of the system 100 can be configured to expand/contract using different technologies and different component configurations. In some embodiments of the system 100, the expansion of the system 100 is achieved through an expansion component 110 that is part of the system 100. In other embodiments, the expansion of the system 100 is achieved by the expansion of a separate component/device in the system 100 that is expanded, and used to then expand or allow for the expansion of the system 100. For example, the removal of a sheath 119 can trigger the expansion of the sheathed balloon 118 in a sheath embodiment 107 of the system 100 (see FIGS. 6a-6g).

Tubular balloons 112 can be implemented in a wide variety of different ways. Some embodiments of tubular balloons 112 as expansion components 110 can use an inflation tube 150 connected to a valve 151 on the tubular balloon 112 to inflate the tubular balloon 112.

Tubular balloons 112 can be inflated using air, other forms of gases, water, and other forms of liquids or fluids. Tubular balloons 112 can also be inflated using mechanical means such as springs. Some embodiments of tubular balloons 112 can involve a balloon 111 that self-inflates.

For tubular balloon embodiments 103 that require active inflation, the valve 151 is typically positioned at the proximal end of the balloon 112, which would be like the 'tail' end of the balloon 112. The valve 151 is connected to an inflation tube 150. The tube 150 runs longitudinally to the inflatable lumen 120. The inflatable lumen is at the distal end, which would be like the 'business' end. The overall length is approximately 100-120 cm (39.4-47.2 inches). The inflatable balloon 112 is approximately 35 mm (1.38 inches). The inflation tube 150 is approximately 65-85 cm (25.6-33.5 inches) in some embodiments of the system 100. The system 100 can be constructed to have a low-profile state 132, which would be a deflated or collapsed state. The low-profile diameter size would be small enough to fit into the required arterial locations and to interface with other medical devices 80 used during the procedure. The low-profile diameter size would be approximately 0.030-0.060 inch (0.76-1.52 mm).

FIG. 3a is a diagram illustrating a partial and close-up view of the system 100 in FIG. 3b. A partial example of the inflatable balloon 112 is illustrated along with the accompanying lumen 120 and the tube 150 that facilitates inflation/deflation.

FIG. 3b is a diagram illustrating an example of an axial view of the system 100. The lumen 120 created by the system 100 is in the form of a "donut hole" at the center of the expansion component 110.

FIG. 3c is a diagram illustrating an example of a top view of the system 100.

FIG. 3d is a diagram illustrating an example of a side view of the system 100.

FIG. 3e is a diagram illustrating an example of a cross-sectional view of a side view of the system 100 with an illustration of a lumen 120 within the system 100.

FIG. 3f illustrates a close-up and partial view of FIG. 3e.

IV. Guide Balloon Embodiments

Some embodiments of the system 100 anticipate that a guide balloon 115 is used in conjunction with the system 100. The guide balloon 115 can help position the system 100 within the body of the patient 90.

Figure 4A:
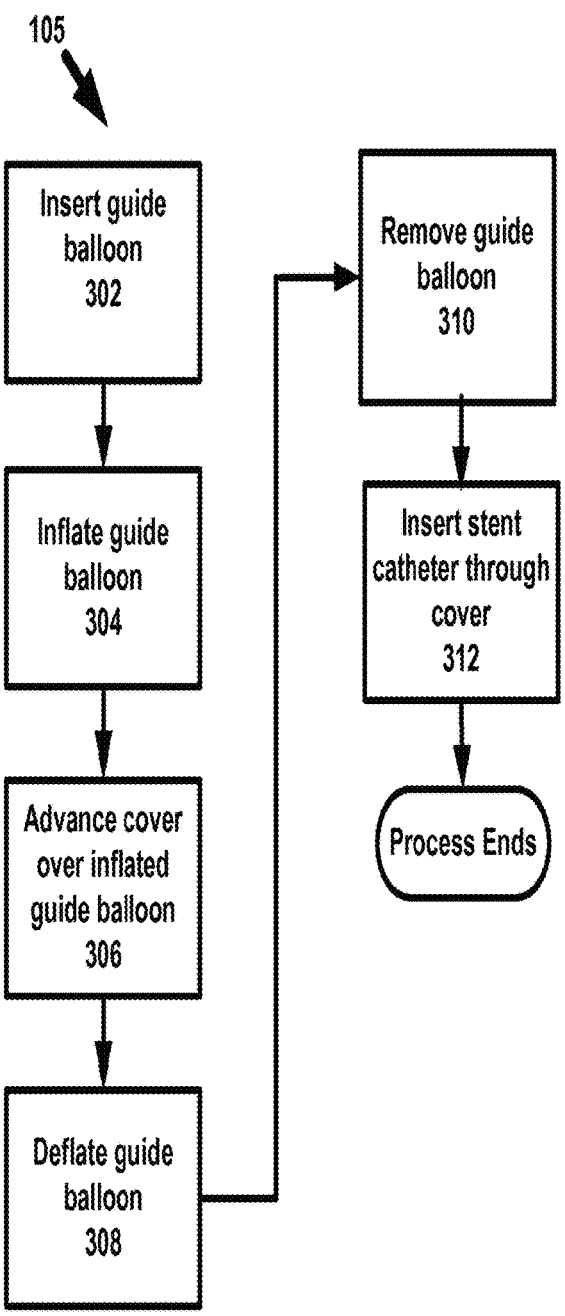
FIG. 4a is a flow chart diagram illustrating an example of a process for creating a lumen using a guide balloon embodiment of the system.

FIG. 4a is a flow chart diagram illustrating an example of a process for enhancing catheterization performed by a guide balloon embodiment 105 of the system 100.

Figure 4B:
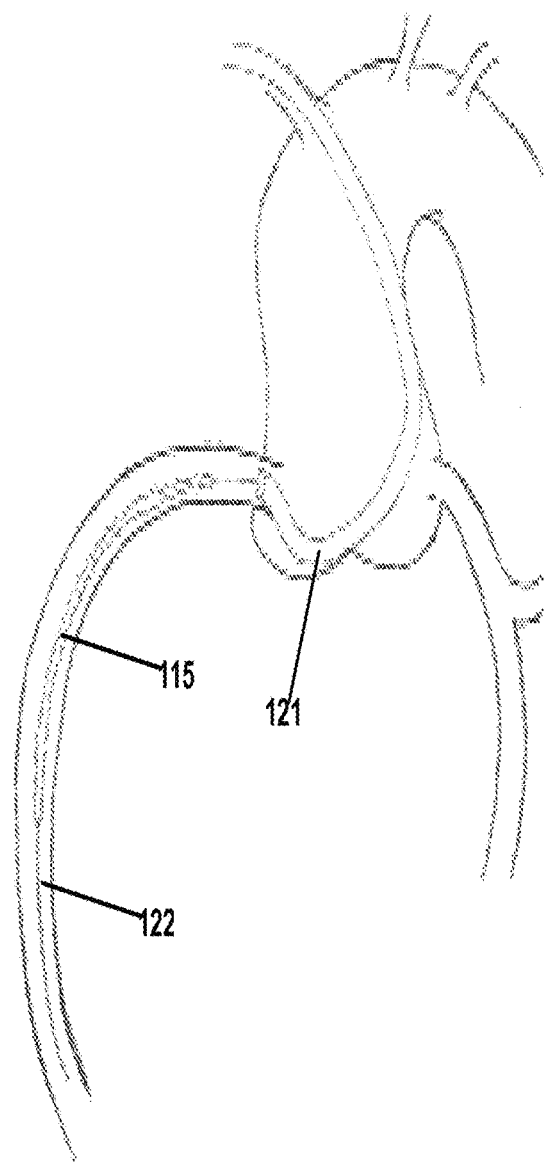
FIG. 4b is an environmental diagram illustrating an example of a process step where the guide balloon is inserted.

At 302, the guide balloon 115 is inserted into the body of the patient 90. FIG. 4b is an environmental diagram illustrating an example of a process step where the guide balloon 115 is inserted. At the beginning of a coronary catheterization procedure a guide catheter 121 or similar medical device 80 can be inserted to the femoral or radial artery, and the guide catheter will be advanced until it accesses the right or left coronary ostium. The ostium is the start of the coronary artery. It is where the artery branches off the aorta. A guide wire 122 will be inserted through the guide catheter 121 and into the coronary artery beyond the point where treatment is to be conducted. The guide balloon 115 of the system 100 will be inserted over top of the guide wire 122 and through the guide catheter 121 into the artery. The guide balloon 115 is in a deflated state while it is inserted. It is inserted past any tortuous areas or stenosis.

Figure 4C:
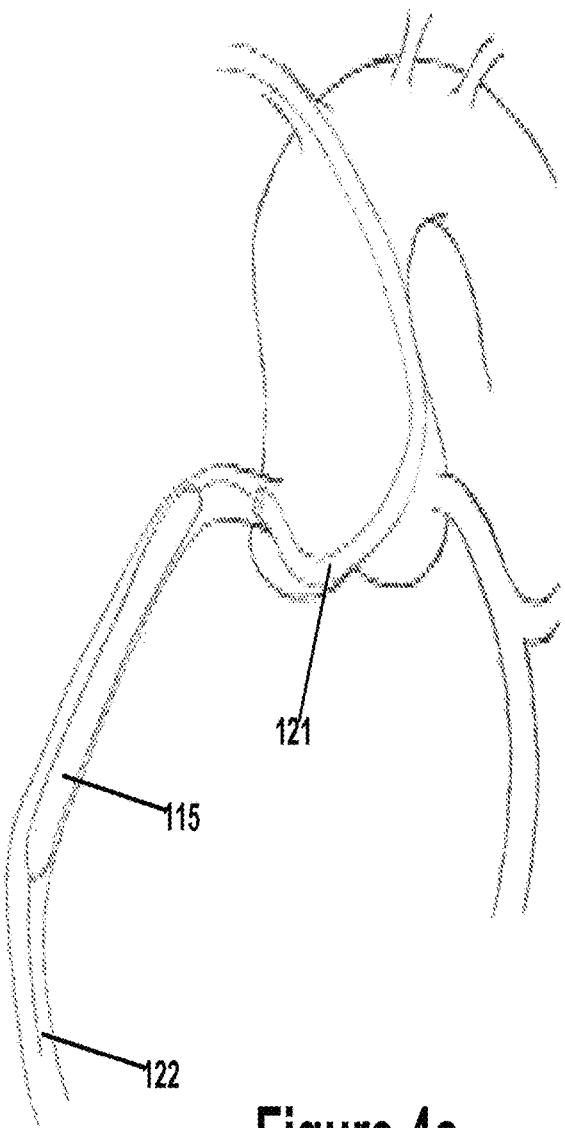
FIG. 4c is an environmental diagram illustrating an example of a process step where the guide balloon is inflated.

Returning to FIG. 4a, at 304 the guide balloon 115 is inflated. FIG. 4c is an environmental diagram illustrating an example of a process step where the guide balloon 115 is inflated. The guide balloon 115 is inflated after it is properly positioned. It can be inflated pneumatically with a gas such as air or hydraulically with a liquid. It is most likely to be inflated which a 50-50 mixture of sterile saline and contrast media. It may be inflated to lower pressures of 1-4 atmospheres or higher pressures up to 16 atmospheres. The inflated outside diameter of the guide balloon 115 may be less than, equal to, or greater than the diameter of the artery. The guide balloon 115 may temporarily straighten any tortuous areas of the artery, either completely or partially.

Figure 4D:
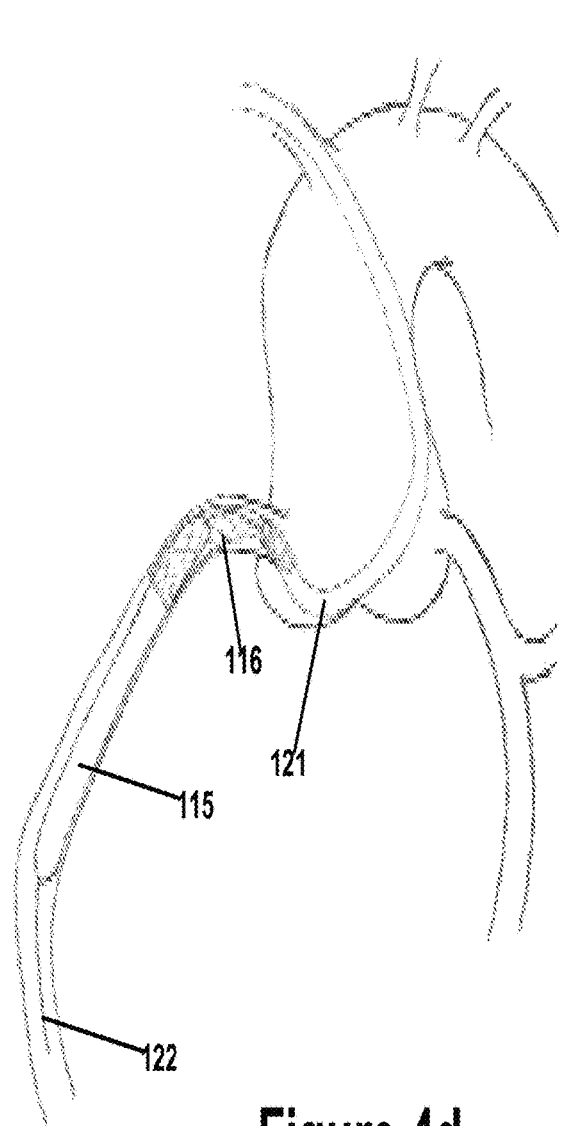
FIG. 4d is an environmental diagram illustrating an example of a process step where the expansion component in the form of a cover is advanced over the inflated guide balloon in order to expand the cover from a low-profile state into a high-profile state.

Returning to FIG. 4a, at 306 the cover 116 is advanced over the guide balloon 115. FIG. 4d is an environmental diagram illustrating an example of a process step where the cover 116 is advanced over the inflated guide balloon 115. The expansion component 110, which is the core component of the system 100, is inserted over top of the guide balloon 115 and through the guide catheter 121. In this embodiment of the system 100 the expansion component 110 may be either a self-expanding design or a fixed diameter design. As the expansion component 110 exists the distal end of the guide catheter 121 it will track over top of the inflated guide balloon 115. The guide balloon 115 outside diameter and the expansion component 110 inside diameter will be specifically designed for an optimum interface. The interface may be a slip fit design, a line-to-line fit design, or an interference design. The interface design will aid insertion of the expansion component 110 and make insertion as atraumatic as possible to eliminate or prevent arterial wall damage.

Figure 4E:
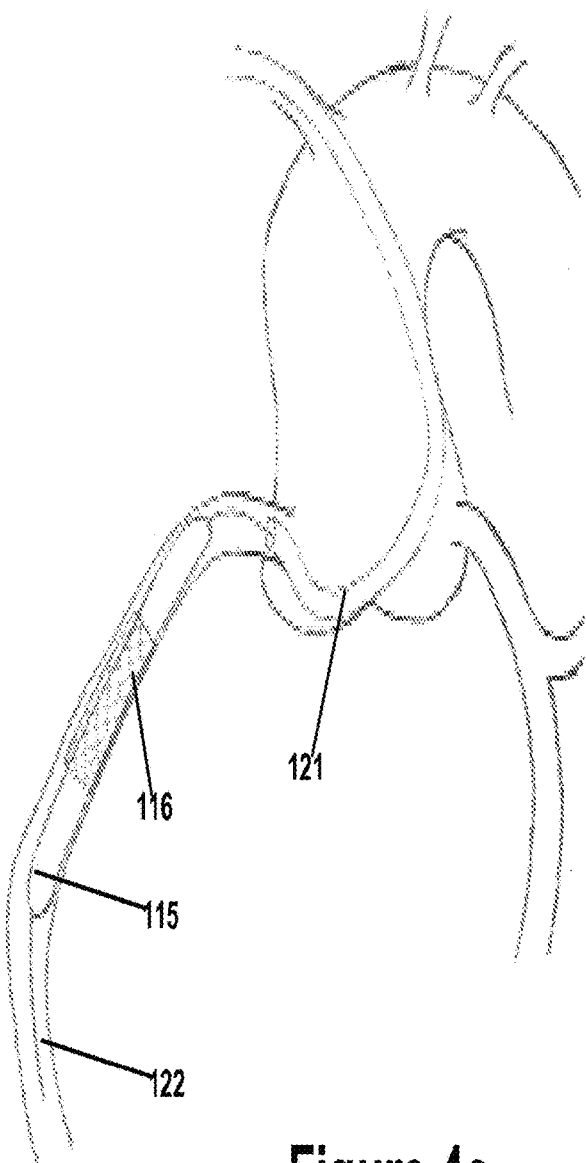
FIG. 4e is an environmental diagram illustrating an example of a process step where the cover is positioned as desired within the body of the patient to create a lumen at the desired location.

FIG. 4e is an environmental diagram illustrating an example of a cover 116 expanded over a guide balloon 115. The guide balloon 115 serves the important task to eliminate or prevent arterial wall damage from the leading edge of the expansion component 110 while it is being inserted, even though the leading edge may be design with its own atraumatic tip. To this end, the guide balloon 115 may intentionally be longer than the expansion component 110. It may be two times or more than the length of the expansion component 110.

Figure 4F:
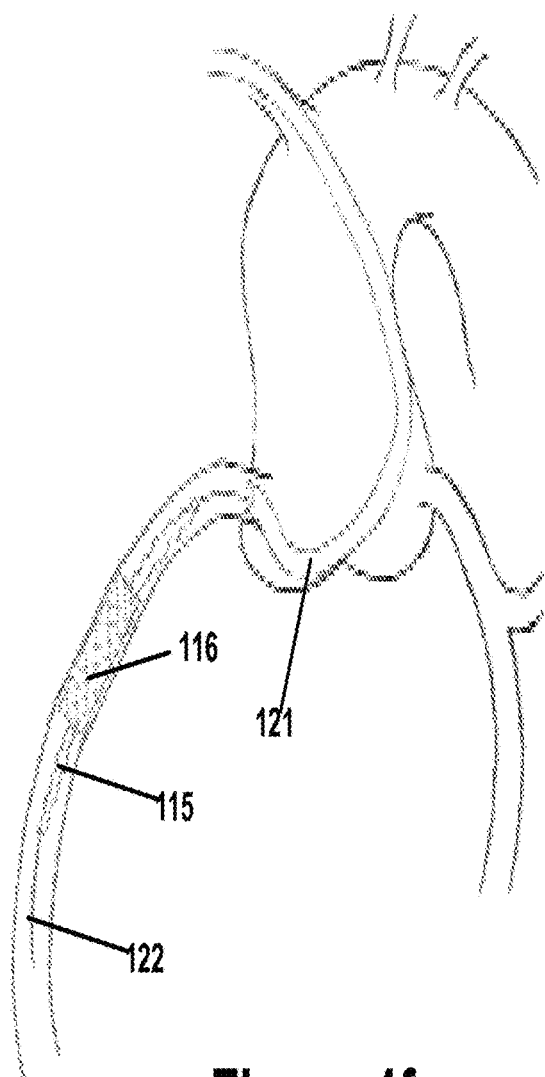
FIG. 4f is an environmental diagram illustrating an example of a process step where the guide balloon is deflated and removed, creating a lumen within the cover.

Returning to FIG. 4a, at 308 the guide balloon 115 is deflated. FIG. 4f is an environmental diagram illustrating an example of a process step where the guide balloon 115 is deflated and removed. The guide balloon 115 is deflated and removed after the expansion component 110 is properly positioned. The expansion component 110 may be designed to maintain straightening of the artery after the guide balloon 115 is removed.

Returning to FIG. 4a, at 310 the guide balloon 115 is removed. The expansion component 110 may be either a self-expanding design or a fixed diameter design for this embodiment of the system 100. The expansion component 110 will create space 120 in the artery in the form of a lumen. Other devices 80 can pass through the space 120 created by the system 100 when it is in the high-profile expanded state 134, such as an angioplasty balloon, a stent catheter, or some other form of similar medical device 80.

Figure 4G:
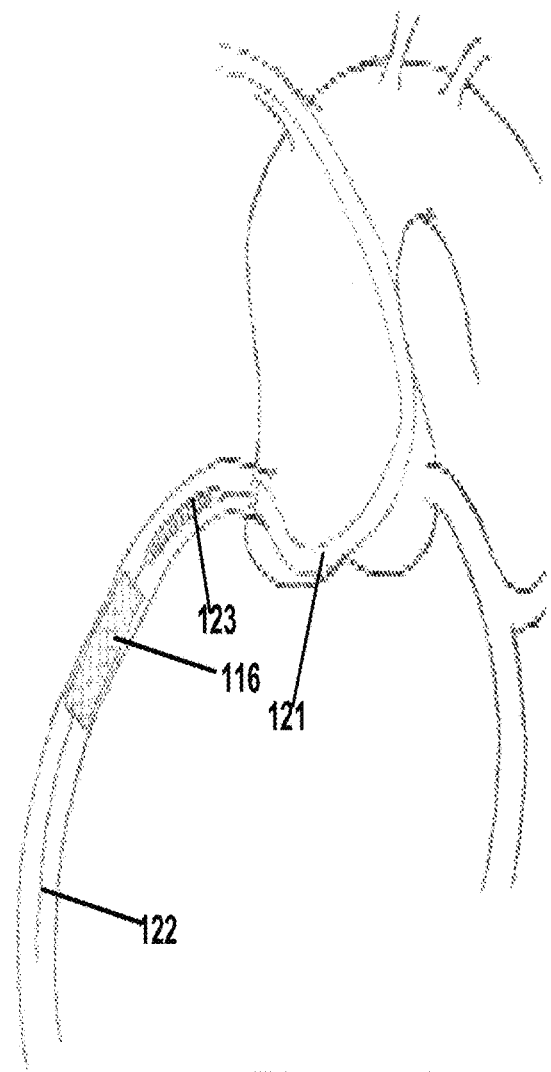
FIG. 4g is an environmental diagram illustrating an example of a process step where a stent catheter is inserted through the space created by the cover.

At 312, a stent 123 is positioned through the system 100. FIG. 4g is an environmental diagram illustrating an example of a process step where a stent 123 is inserted through the space 120 created by the system 100.

The system 100 is removed from the artery when it is not needed anymore. The artery would regain its natural shape. This embodiment of the system 100 would interface with the other catheterization devices 80 used during the procedure, such as the guide wire 122, guide catheter 121, balloon catheters and stent 123.

V. Insertion Component Embodiments

FIG. 5a is a flow chart diagram illustrating an example of a process for enhancing catheterization performed by an insertion component embodiment 106 of the system 100. This embodiment of the system 100 uses an insertion component 117 that is inserted into the expansion component 110 of a cover 116. In some embodiments, the insertion component 117 can be attached to the guide catheter 121.

At 322, the cover 116 attached to the guide catheter 121 is inserted into the body of the patient 90. FIG. 5b is an environmental diagram illustrating an example of a process step where the cover 116 is inserted into the body of the patient 90. At the beginning of a typical coronary catheterization procedure a guide catheter 121 will be inserted to the femoral or radial artery, and the catheter 121 will be advanced until it accesses the right or left coronary ostium. The ostium is the start of the coronary artery. It is where the artery branches off the aorta. A guide wire 122 will be inserted through the guide catheter 121 and into the coronary artery beyond the point where treatment is to be conducted. For this embodiment of the expansion component 110, which is in the form of a cover 116, the cover 116 will often be an integral part of the guide catheter 121. The cover 116 can be connected to the distal end of the guide catheter 121 as pat of the manufacturing process for those components.

Figure 5C:
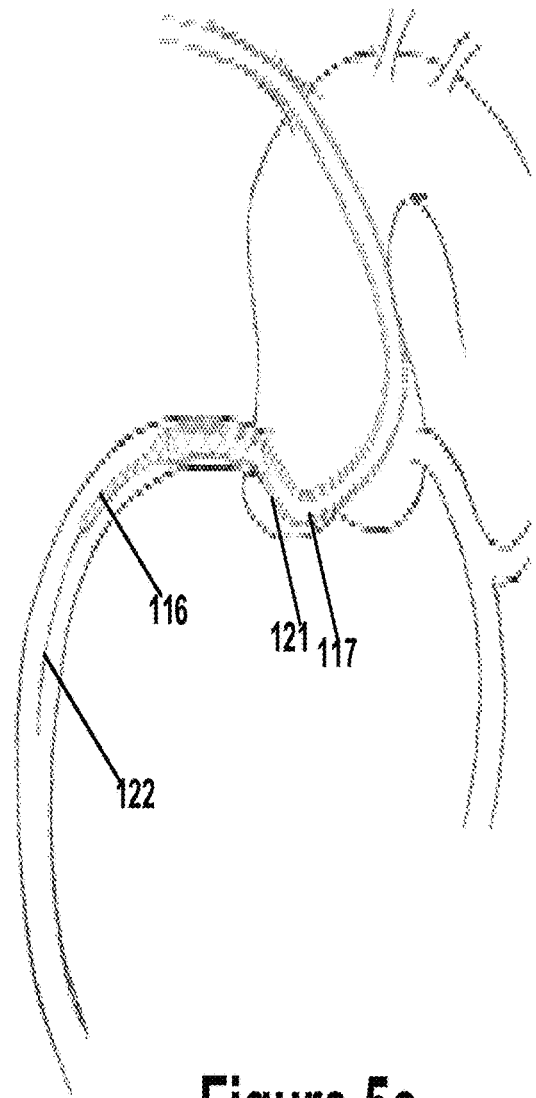
FIG. 5c is an environmental diagram illustrating an example of a process step where an insertion component is inserted into the cover (a type of expansion component) positioned within the body of the patient to expand the distal section of the expansion component and to create the desired lumen at the desired location.

Returning to FIG. 5a, at 324 an insertion component 117 is inserted into the cover 116. FIG. 5c is an environmental diagram illustrating an example of a process step where an insertion component 117 is inserted into the cover 116 positioned within the body of the patient 90 to expand the distal section of the cover 116. An insertion component 117 would be inserted into the inside the entire length of the connected expansion component 110 (i.e. the cover 116) and guide catheter 121. As it is inserted it will expand the expansion component 110 (i.e. the cove 116) to the high-profile state 134.

Figure 5D:
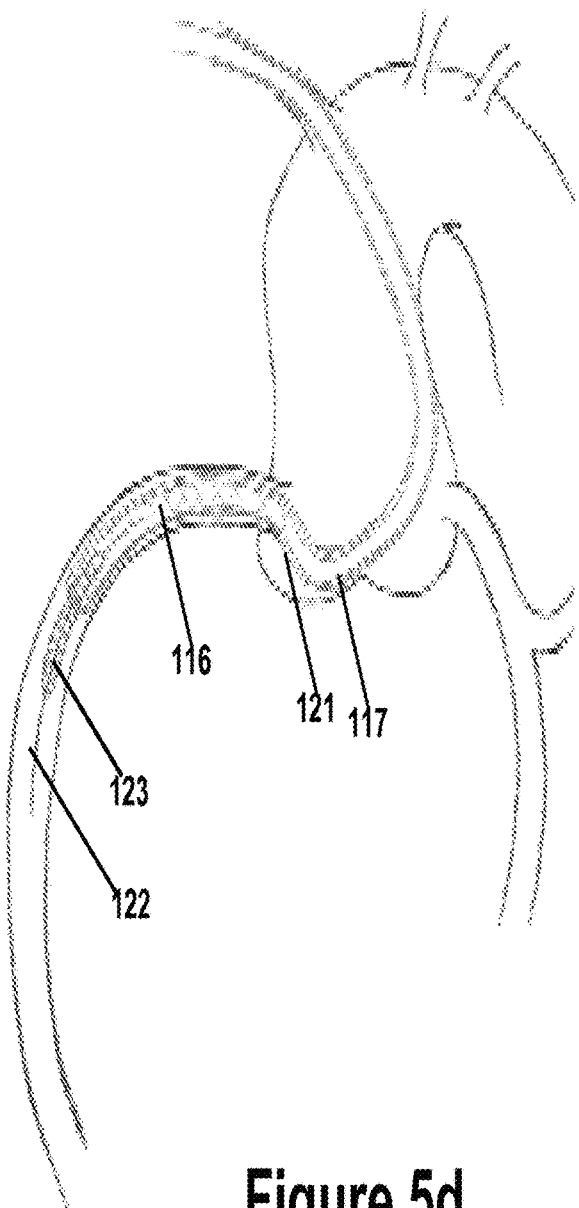
FIG. 5*d* is an environmental diagram illustrating an example of a process step where a stent catheter is inserted through the cover.

Returning to FIG. 5a, at 326 a stent catheter 123 is inserted into the body of the patient 90 through the insertion component 117. FIG. 5d is an environmental diagram illustrating an example of a process step at 326. The nested structure of the high-profile state 134 expansion component 110 and the insertion component 117 will create space 120 through which other medical devices 80 can be inserted, such as an angioplasty balloon catheter or a stent catheter 123.

The expansion component 110 (i.e. the cover 116) of the system 100 and insertion component 117 will be removed when they are not needed anymore.

The expansion component 110 of this embodiment can be made with shape memory materials, a braid construction, a pleated design or any other expandable design structure.

Shape memory materials can be metallic or non-metallic. Nitinol is one possible metallic material that could be used. The expansion component 110 could be made from Nitinol and the memorized shape would be the low-profile state 132. This memorized low-profile state 132 would enable the connected expansion component 110 and guide catheter 121 to be inserted into the coronary artery past the ostium, tortuous areas and any stenoses. The insertion component 117 would be used to actively transition the expansion component 110 from the low-profile state 132 to the high-profile state 134. Non-metallic shape memory polymers could also be used to construct the expansion component 110 and accomplish the same result.

A braid structure could be used to construct the cover 116. The braid would be made to the size of the low-profile state 132. The woven mesh pattern of the braid has space in the interstices between its wires. This would allow it to expand to the high-profile state 134 when the insertion component 117 is inserted.

A pleated design could be used to make the cover 116. The pleated design would be made to the size of the low-profile state 132. The insertion component 117 would unfold the pleats, when it is inserted, allowing it to transition to the high-profile state 134.

VI. Sheathed Balloon Embodiments

Figure 6A:
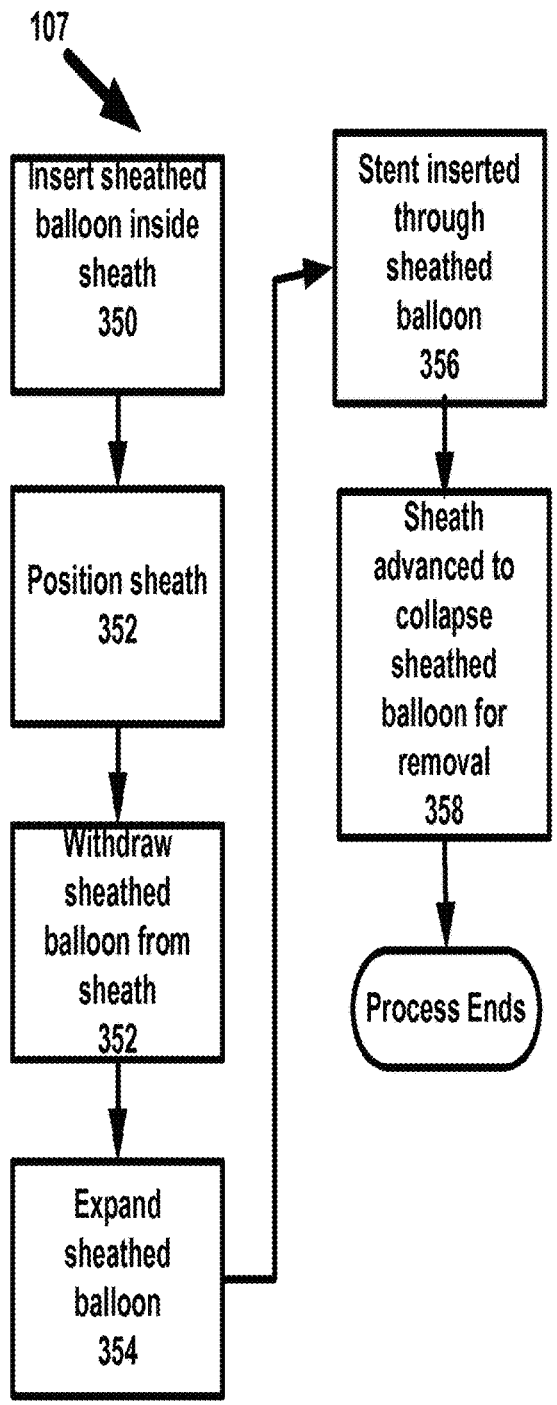
FIG. 6*a* is a flow chart diagram illustrating an example of a process for creating a lumen using a sheathed balloon embodiment of the system.

FIG. 6a is a flow chart diagram illustrating an example of a process of enhancing catheterization performed by a sheath covered embodiment 107 of the system 100. In this category of embodiments, expansion component 110 of the system 100 is self-expanding. The sheath 119 allows for the expansion component 110 to exist in a low-profile mode 132 by constraining the expansion component 110. Once the expansion component 110 is released from the sheath 119, the expansion component 110 (such as a sheathed balloon 118) expands into a high-profile operating mode 134.

The self-expanding feature can be made with self-expanding materials, such as a braid structure. The braid structure is cylindrical in shape. The wall of the cylinder is constructed of the woven mesh of the braid. The ends of the cylinder are open. The braid would be designed with space in its weave pattern, which would allow the braid structure to exist in either the high-profile self-expanded state 134 or the low-profile state 132.

Figure 6B:
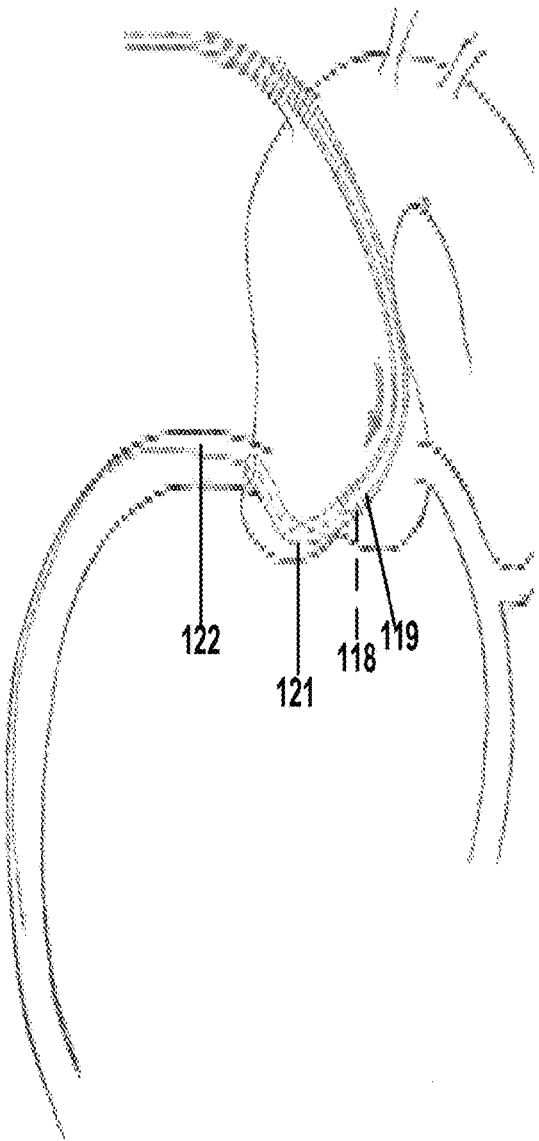
FIG. 6*b* is an environmental diagram illustrating an example of a process step where a sheath covers the sheathed balloon during insertion the sheathed balloon.

At 350, the system 100 with sheath 119 (and the encapsulated expansion component 110 such as a sheathed balloon 118) is inserted into the body of the patient 90. FIG. 6b is an environmental diagram illustrating an example of a process step where a sheath 119 covers the system 100 during insertion. The expansion component 110 could be compressed to a low-profile state 132 and inserted into a sheath 119. The sheath 119 would cover the expansion component 110 keeping it in the low-profile state 132. The expansion component 110 and sheath 119 would be inserted through the guide catheter 121 and into the artery 91 as one unit.

Figure 6C:
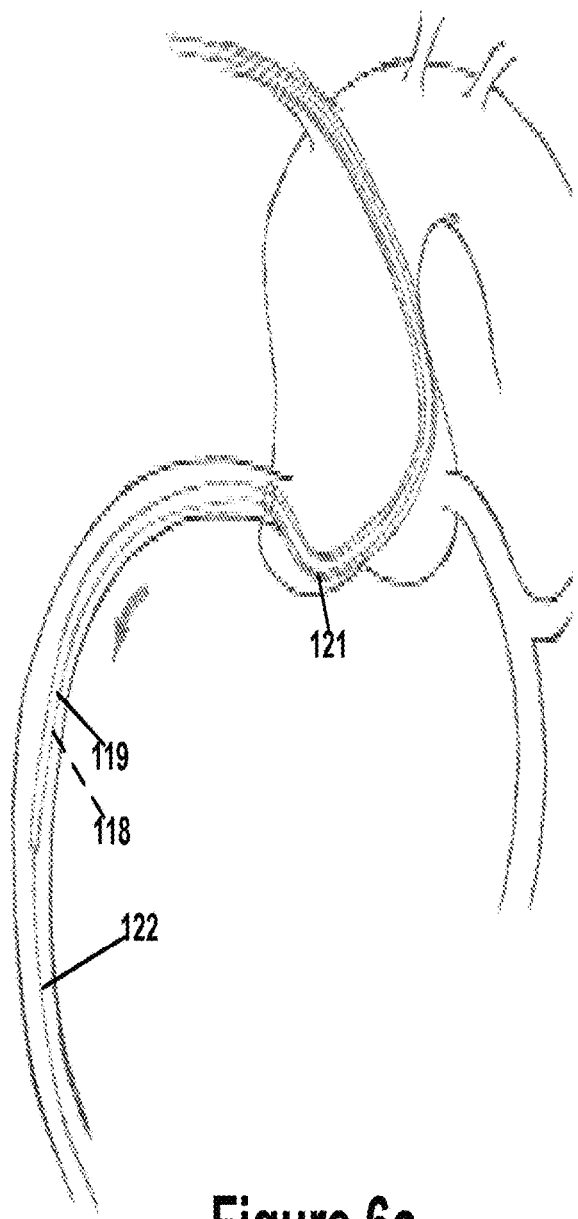
FIG. 6*c* is an environmental diagram illustrating an example of a process step where the sheath and the sheathed balloon within the sheath are positioned as desired within the body of the patient.
Figure 6D:
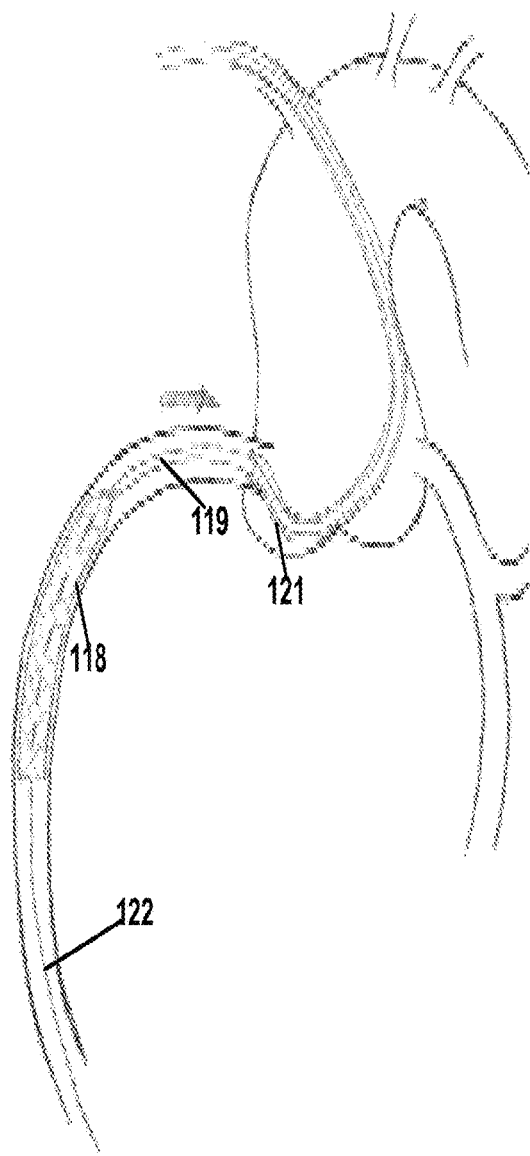
FIG. 6*d* is an environmental diagram illustrating an example of a process step where the sheath is withdrawn. This causes the balloon to self-expand because it is no longer constrained by the sheath, triggering the creation of the additional working space (i.e. lumen) within in the body of the patient.

Returning to FIG. 6a, at 352 the system 100 is positioned within the body of the patient 90. FIG. 6c is an environmental diagram illustrating an example of a process step where the sheath 119 and system 100 are positioned as desired within the body of the patient 90. The expansion component 110 and sheath 119 would have an appropriate low-profile size, strength, and flexibility to be inserted past any tortuous areas or stenosis Returning to FIG. 6a, at 352 the sheath 119 is withdrawn. FIG. 6d is an environmental diagram illustrating an example of a process step where the sheath 119 is withdrawn; causing the system 100 to self-expand and triggering the creation of the additional working space 120 within in the body of the patient 90 for the purposes of catheterization. The sheath 119 is removed after the system 100 is properly positioned. The expansion component 110 will automatically deploy because of its self-expanding feature. The expansion component creates space 120 in the artery.

Returning to FIG. 6a, at 354 the system 100 is expanded into a high-profile state 134. FIG. 6e is an environmental diagram illustrating an example of how the expanded system 100 can straighten out an artery within the body of the patient 90. The expansion component 110 may partially or completely straighten any artery tortuosity. The straightening effect would be transient. When the system 100 is withdrawn the artery would regain its natural shape Returning to FIG. 6a, at 356 the stent catheter 123 is inserted through the system 100. FIG. 6f is an environmental diagram illustrating an example of a process step where the stent catheter 123 is inserted into the patient 90 through the working space 120 created by the presence of the system 100 in a high-profile operating mode 134. Other devices can pass through the space 120 created by the system 100 when it is in the high-profile expanded state 134, such as an angioplasty balloon catheter or stent 123.

Figure 6G:
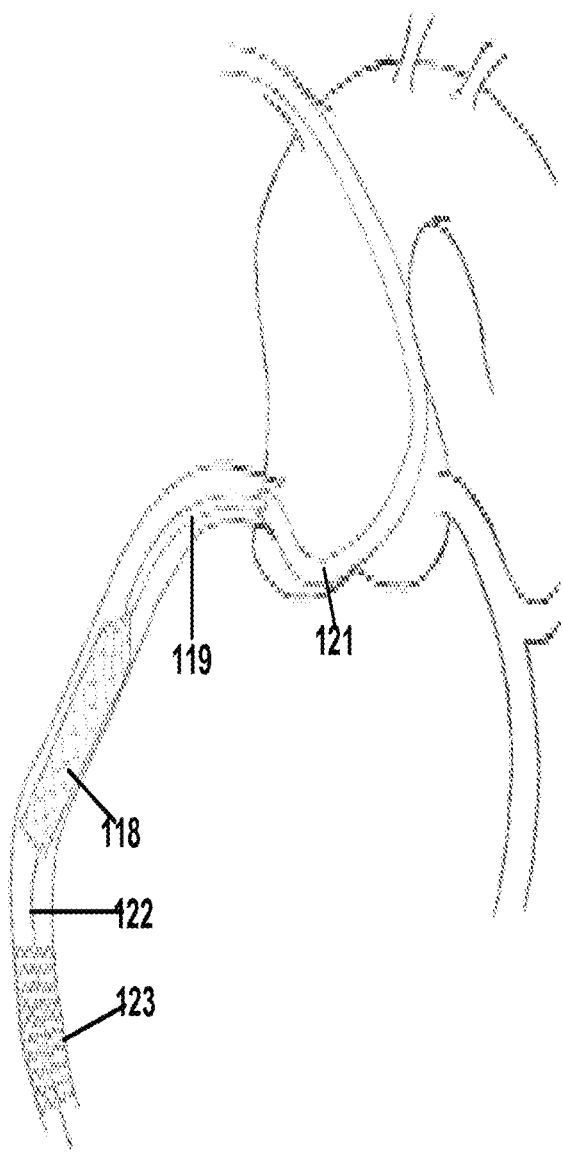
FIG. 6*g* is an environmental diagram illustrating an example of a process step where the sheath is advanced to collapse the balloon for removal.

Returning to FIG. 6a, at 358 the sheath 119 is advanced to collapse the system 100 for removal. FIG. 6g is an environmental diagram illustrating an example of a process step where the sheath 119 is advance to collapse the system 100 for removal. The system 100 can be removed when it is not needed any more. The sheath 119 is advanced over the expansion component 110 causing it to collapse to the low-profile state 132, and then the expansion component 110 and sheath 119 are removed together as one unit.

An alternate embodiment of this form of the system 100 uses a self-expanding braid structure 124 to serve as the sheathed balloon 118. The construction of the braid 124 can be designed to provide optimum performance. Braid 124 characteristics such as number of wires, shape of wire, wire material, pitch, uniform pitch, variable pitch and weave pattern can be chosen to obtain the desired performance. More or less wires, and wire material, can affect strength and flexibility of the component. Round wires or flat wires can affect wall thickness. Pitch and weave pattern can affect expansion strength and profile size.

Stainless Steel or Nitinol are likely materials for the braid 124 wire, however other metals or non-metals can possibly be used. Stainless Steel can be formulated with 'spring' characteristics enabling it to self-expand. Nitinol is a metallic alloy of nickel and titanium. It is in a class of metals known as 'shape memory'. A nitinol-based expansion component can be made with a shape memory of the high-profile expanded state 134, enabling it to self-expand. There are also shape memory polymers that can be used to construct the expansion component.

The braid 124 can be covered with an inner and outer liner to make it atraumatic and prevent arterial wall damage. The inner and outer liners would expand and collapse with the system 100.

The sheath 119 may have an atraumatic tip to aid insertion and eliminate or reduce damage to the artery wall.

The expansion component 110, sheath 119 or both items could have radio-opaque features so they can be visualized with fluoroscopic imaging.

This embodiment of the system 100 can interface with the other catheterization devices used during the procedure, such as the guide wire 122, guide catheter 121, balloon catheters, stent 123, as well as other medical devices 80.

VII. Helix Balloon Embodiments

Helix balloon embodiments 104 of the system 100 are similar to tubular balloon embodiments 103 of the system 100, except that in a helix balloon embodiment 104 of the system 100, the balloon 111 is constrained and shaped by a matrix 114 the configures the shape of the balloon 111 into a helix balloon 113.

A. Helix Balloon

Just as a tubular balloon 112 can be inflatable, self-inflating, or mechanically expanding, a helix balloon 113 can change operating modes 130 in precisely the same ways using the same technologies and principles of chemistry and physics.

B. Matrix

A mechanism or configuration of mechanisms that keep the balloon 111 in the shape of a helix balloon 113. The matrix 114 maintains the helical shape of the helix balloon 113 in all operating modes 130. The matrix 114 can be implemented in a wide variety of different embodiments, including but not limited to a weave 145, a bonding agent 146, a thermally formed connection 147, a matrix cover 148, and a flange 149. The cross sectional shape of the helix balloon 113 can be maintained differently in different operating modes 130. For example, the cross section of the helix balloon 113 would otherwise be round in an inflated state (high-profile operating mode 134) and flat in a deflated state (low-profile operating mode 132). The matrix 114 can maintain the helical shape in both states. The matrix 114 needs both flexibility and strength to properly perform its function.

The matrix 114 can include a medicinal component 126, a mechanism or configuration of mechanisms that enable medicinal capabilities to the system 100. The medicinal component 126 may include diagnosis or treatment of a medical condition, or delivery of medicine or nutrient. The matrix 114 may contain vaso-active agents to cause vaso-constriction or vasodilation, depending on what may be required. Such an agent may be transient or longer lasting. Nitric oxide is an example of a vaso-active agent that can dilate a vessel, which would make the vessel bigger (larger diameter) until the agent wears off. The matrix 114 may contain any of the class of drug coatings that prevent intimal hyperplasia. Intimal hyperplasia often is a physiologic response to an angioplasty procedure resulting in restenosis of the treated area, which in layman's terms is a clogged stent 123.

1. Weave

A weave 145 can be a configuration of one or more threads 144 that can contain the balloon 111 in the shape of a helix balloon 113. The weave 145 can use as many or as few threads 144 as desired. In many embodiments, between 10-12 threads 144 uniformly distributed about the helix balloon 113 is a particular desirable configuration. The weave 145 would wrap around the helix balloon 113 as the helix balloon 113 makes consecutive passes of the helical shape.

2. Bonding Agent

A chemical means to constrain the shape of the helix balloon 113. The matrix 114 can be made from a bonding agent 146 that is applied to a balloon 111 to secure its shape as a helix balloon 113. A bonding agent 146 can be used by itself or with other components to maintain the helical shape of the helix balloon 113. Consecutive passes of the helical shape can be bonded to adjacent passes. A wide variety of bonding agents including but not limited to adhesive glues or silicone can be used as possible bonding agents 146. The bonding agent 146 may be applied using dip coating techniques.

3. Thermally Formed Connection

A constraint on the helix balloon 113 that is implemented through the application of heat. A wide range of thermal forming techniques known in the prior art can be used to connect adjacent passes of the helical shape together. The aggregate configuration of thermally formed connections 147 can by itself or in conjunction with other components, constitute the matrix 114.

4. Matrix Covering

A matrix cover 148 is a relatively thin sheet or a collection of thin sheets that overlay the balloon 111 to shape it into a helix balloon 113. The matrix cover 148 can contain the helix balloon 113 and maintain its helical shape. The matrix cover 148 can be made from a fabric or other similar material suitable for the particular location 88 in the patient 90. The matrix cover 148 can cover a single pass of the helical shape, multiple passes or all passes. The matrix cover 148 can be used by itself or in conjunction with other components to constitute the matrix 114. The matrix cover 148 may be applied using dip coating techniques as well as other plausible manufacturing methods.

5. Flange

A flange 149 is a rim, collar, or ring that secures the balloon 111 into the shape of a helix balloon 113. The cross-section of the helix balloon 113 can have one or more flanges 149. Adjacent passes of the helical shape can be connected together by the flange 149. The connected flanges 149 in the aggregate can form the matrix component 114. Flanges 149 can be connected using a weave 145, a bonding agent 146, a thermally formed connection 147, a matrix cover 148, and/or potentially other means.

C. Examples

Figure 7A:
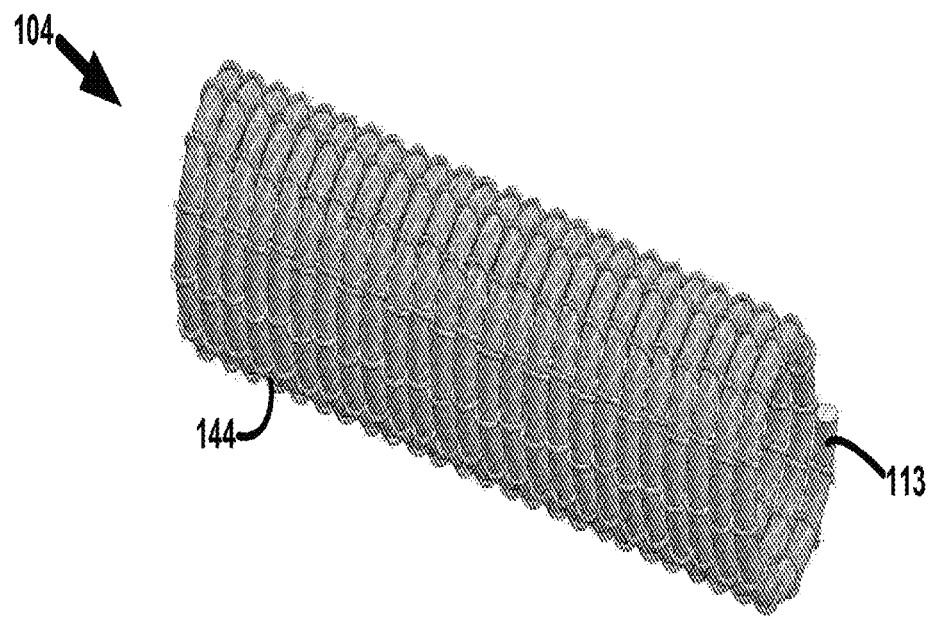
FIG. 7*a* is a diagram illustrating a perspective view of a helix and matrix configuration that includes a tubular balloon constrained in the shape of a helix by a weave functioning as a matrix.

FIG. 7a is a diagram illustrating a perspective view of a helix 113 and matrix 114 configuration that includes a tubular balloon constrained in the shape of a helix by a weave 145 functioning as a matrix 114. The central lumen 120 inside the helix is 0.058 inches, which is created by wrapping the tubular balloon 112 around a mandrel and secured by the matrix 114. Twelve threads 144 that are 0.002 inches in diameter form the matrix 114.

Figure 7B:
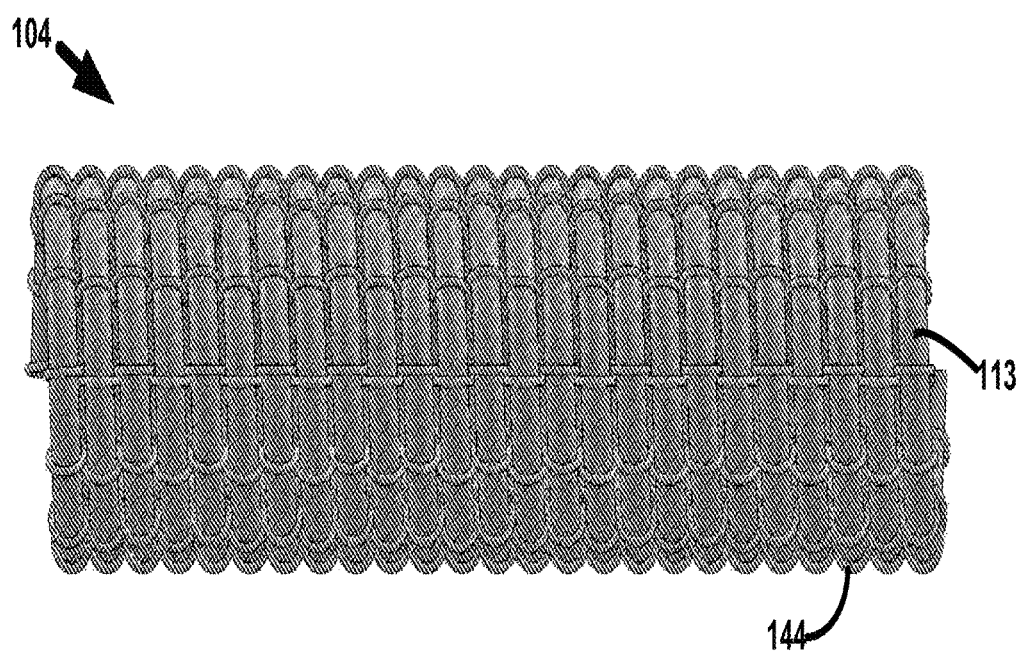
FIG. 7*b* is a diagram illustrating an example of a side view of the helix and matrix configuration of FIG. 7*a*.

FIG. 7b is a diagram illustrating an example of a side view of the helix 113 and matrix 114 configuration of FIG. 7a.

Figure 7C:
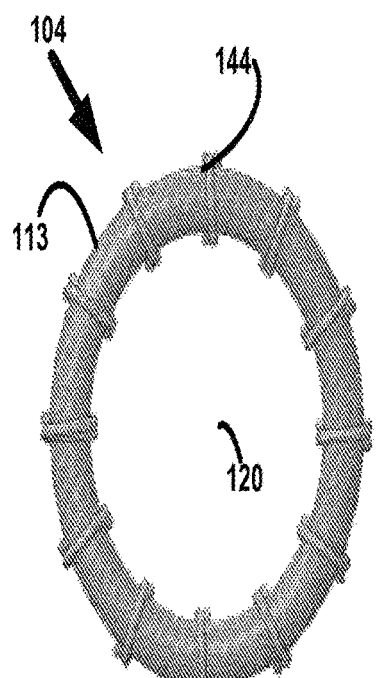
FIG. 7*c* is a diagram illustrating an example of an axial view of the helix and matrix configuration of FIGS. 7*a* and 7*b*.

FIG. 7c is a diagram illustrating an example of a planar front view of the helix 113 and matrix 114 configuration of FIGS. 7a and 7b. As illustrated in the figure, the 12 threads are uniformly spaced around the helix balloon 113.

Figure 7D:
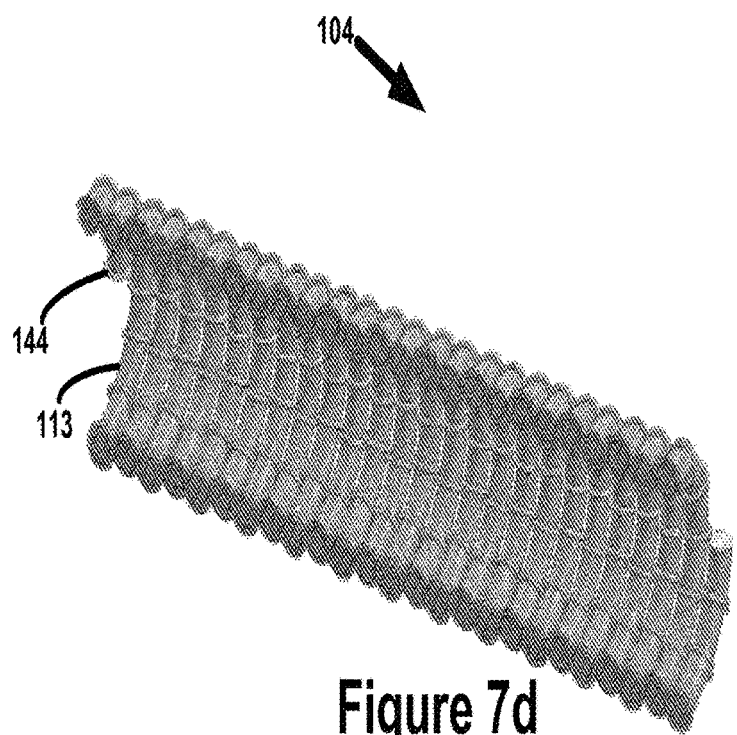
FIG. 7*d* is a diagram illustrating an example of a perspective section view of the helix and matrix configuration of FIGS. 7*a*-7*c*.

FIG. 7d is a diagram illustrating an example of a perspective section view of the helix 113 and matrix 114 configuration of FIGS. 7a-7c.

Figure 7E:
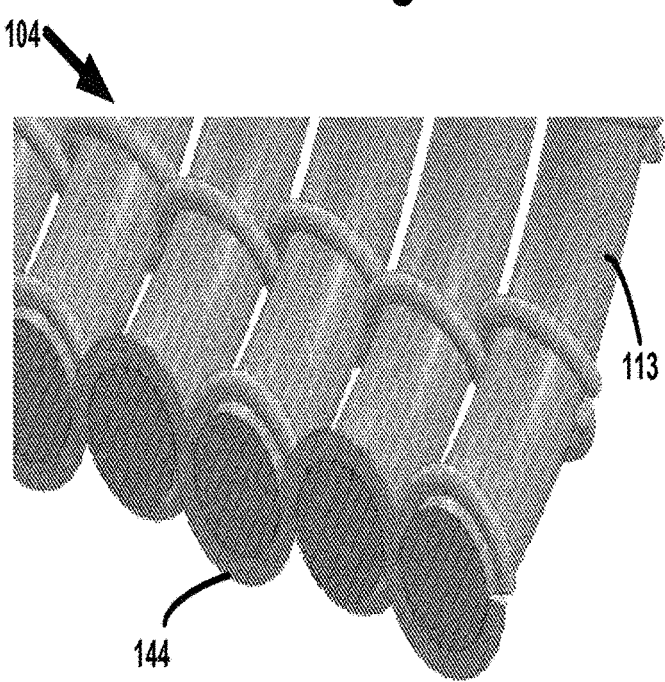
FIG. 7*e* is a diagram illustrating an example of close-up view of the illustration in FIG. 7*d*.

FIG. 7e is a diagram illustrating an example of a close-up view of the illustration in FIG. 7d.

Figure 7F:
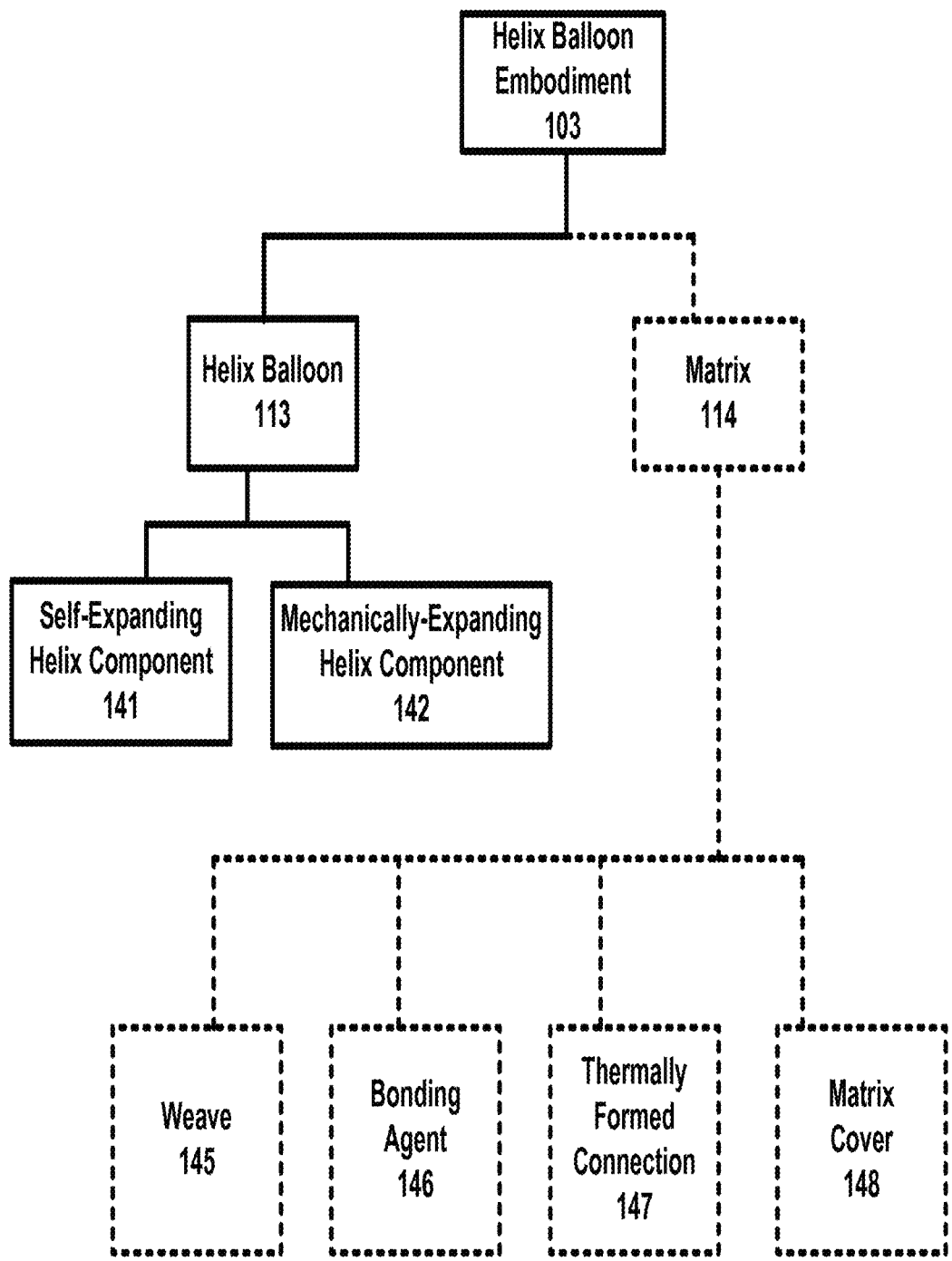
FIG. 7*f* is a hierarchy diagram illustrating an example of different components and component configurations that can be utilized in a helix balloon embodiment of the system.

FIG. 7*f* is a hierarchy diagram illustrating various examples of different helix balloon 113 and matrix components 114. As illustrated by the dotted line in the figure, the matrix 114 is an optional component although often a highly desirable one. As illustrated in the Figure, a helix balloon 113 can be implemented as a self-expanding helix component 141, a mechanically-expanding helix component 142, as well as the inflatable helix balloon 113 illustrated in FIGS. 7*a*-7*e*. As illustrated in the Figure, the matrix 114 can be implemented as a weave 145, a bonding agent 146, a thermally formed connection 147, and a matrix cover 148. As discussed above, the matrix 114 can include a medicinal component 126.

VIII. Glossary/Index

Table 1 below is a chart linking together element numbers, element names, and element descriptions.

TABLE 1

| # | Name | Description |
|---|------|-------------|
| 80 | Medical Device | A device that serves a medical purpose within the body of the patient 90. The system 100 creates the lumen 120 in order to provide space for the medical device 80 to be positioned at a desired location 88 within the body of the patient 90. |
| 81 | Medical Procedure | A process performed on or in a patient 90 by a provider 92 for the purpose of benefiting the health status of the patient 90. Examples of medical procedures 81 that can benefit from the creation of a lumen 120 or the enhancement of a lumen 120 can include but are not limited to Percutaneous Coronary Intervention (PCI), Percutaneous Coronary Angiogram (PCA), Chronic Total Occlusions (CTO), Stent implantation, Atherectomy, and Embolic Protection. Although the system 100 was originally devised to assist providers 92 with respect to coronary vascular procedures, the system 100 can benefit patients 90 in other contexts. |
| 88 | Desired Location | A position within the body of the patient 90 that the provider 92 desires to create a lumen 120 for the insertion of a medical device 80 and/or the performance of a medical procedure 81. |
| 90 | Patient | The beneficiary of the medical device 80. The patient 90 is the organism in which the lumen 120 is created for the purposes of positioning and utilizing the medical device 80. The system 100 can be used with respect to a wide variety of different types of patients 90 including but not limited to, human beings, other types of mammals, other types of animals, and other living organisms. |
| 91 | Blood Vessel | A passageway in the body of the patient 90 through which blood circulates. |
| 92 | Provider | A person who provides health care assistance to the patient 90. The provider 92 is typically a physician 92, but other professionals such as nurses, paramedics, physician assistants, etc. may also act as providers 92 with respect to the system 100. |
| 100 | System | A collection of components that collectively provide for the functionality of creating a space 120 within a body. |
| 101 | Direct Expansion Embodiments | Embodiments of the system 100 that directly inflate or deflate the expansion component 110 in order to change operating modes 130. Direct expansion embodiments 101 can include but are not limited to a balloon 111, such as a tubular balloon embodiments 103 and helix balloon embodiments 104. |
| 102 | Indirect Expansion Embodiments | Embodiments of the system 100 that utilize other components of the system 100 to expand or shrink the expansion component 110. Indirect expansion embodiments 102 can include but are not limited to guide balloon embodiments 105 (expansion component 110 expands by advancing on a guide balloon 115), insertion component embodiments 106 (expansion component 110 expands by the insertion of an insertion component 117), and sheathed balloon embodiments 107 (expansion component 110 expands when it is removed from and no longer constrained by the sheath 119). |
| 103 | Tubular Balloon Embodiments | An embodiment of the system 100 where the expansion component 110 is a tubular balloon |
| 104 | Helix Balloon Embodiments | An embodiment of the system 100 where the expansion component 110 is a helix balloon. |
| 105 | Guide Balloon Embodiments | An embodiment of the system 100 where a the expansion component 110 is advanced over a guide balloon 115 (which is a type of balloon 111) that is in an inflated state in order to expand the expansion component 110 from a low-profile operating mode 132 into a high-profile operating mode 134. |
| 106 | Insertion Component Embodiments | An embodiment of the system 100 where an insertion component is inserted into the expansion component 110 to expand the expansion component 110 from a low-profile operating mode 132 into a high-profile operating mode 134. |
| 107 | Sheathed Balloon Embodiments | An embodiment of the system 100 where a sheathed balloon 118 is removed from a sheath 119 to change from a low-profile operating mode 132 into a high-profile operating mode 134. The sheathed balloon 118 expands when no longer constrained by the sheath 119. |

TABLE 1-continued

| # | Name | Description |
|---|---|---|
| 108 | Expansion Component Balloon Embodiments | Embodiments of the system 100 that involve some type of a balloon 111 as the expansion component 110. Examples of expansion component balloon embodiments 108 can include but are not limited to tubular balloon embodiments 103, helix balloon embodiments 104, and sheath embodiments 107. |
| 109 | Expansion Component Non-Balloon Embodiments | Embodiments of the system 100 that do not involve an expansion component 110 that is a balloon 111. Examples of expansion component non-balloon embodiments 109 can include but are not limited to guide balloon embodiments 105 (expansion component 110 is advanced onto an inflated guide balloon 115) and insertion component embodiments 106 (insertion component 117 such as a second guide catheter 121 is inserted into the expansion component 110). |
| 110 | Expansion Component | Potentially any mechanism that can expand from a low-profile operating mode 132 into a high-profile operating mode 134 to create the space 120. |
| 111 | Balloon | An at least semi-flexible container, such that filling the container changes the shape of the container. Balloons can be inflated with air, other types of gasses, water, and other types of liquids. Some embodiments of balloons 111 can be inflated utilizing mechanical means. Many categories of expansion components 110 are balloons 111 (tubular balloon embodiments 103, helix balloon embodiments 104, and sheathed balloon embodiments 107) or are used in conjunction with balloons 111 (guide balloon embodiments 105). |
| 112 | Tubular Balloon | A balloon 111 with a "donut hole" in the center of the balloon 111. When the tubular balloon 112 is inflated, the "donut hole" at the center of the balloon 111 is the lumen 120. |
| 113 | Helix Balloon | A balloon 111 that is helix or helical shaped, like a coil or spring. The center of the helix can be used to create a lumen 120 when the helix balloon 113 expands from a low-profile state 132 into a high-profile state 134. The helix balloon 113 may be coupled with a matrix 114 to reinforce and augment the desired shape and structural attributes of the helix balloon 113. |
| 114 | Matrix or Matrix Component | A mechanism or configuration of mechanisms that keep the balloon 111 in the shape of a helix balloon 113. The matrix 114 maintains the helical shape of the helix balloon 113 in all operating modes 130. The matrix 114 can be implemented in a wide variety of different embodiments, including but not limited to a weave 145, a bonding agent 146, a thermally formed connection 147, a cover 148, and a flange 149. The cross sectional shape of the helix balloon 113 can be maintained differently in different operating modes 130. For example, the cross section of the helix balloon 113 would otherwise be round in an inflated state (high-profile operating mode 134) and flat in a deflated state (low-profile operating mode 132). The matrix 114 can maintain the helical shape in both states. The matrix 114 needs the both flexibility and strength to properly perform its function. The matrix 114 can also be referred to as a matrix component 114. |
| 115 | Guide Balloon | The balloon 111 used in conjunction with a cover 116 to change the cover 116 from a low-profile operating mode 132 into a high-profile operating mode 134. |
| 116 | Cover | The expansion component 110 can be implemented as a cover 116 to the guide balloon 115 or to the insertion component 117. In the context of an insertion component embodiment 106, the cover 116 can be an integral part of a customary guide catheter 121 in the form of an extension on the distal end of the guide catheter 121. In many such embodiments, the cover 116 can be permanently and irremovably attached from the guide catheter 121 at the time of manufacture. The cover 116 can also be referred to as an expandable cover. |
| 117 | Insertion Component | A device that is inserted into the expansion component 110 to trigger the expansion of the expansion component 110 from a low-profile operating mode 132 into a high-profile operating mode 134. In some embodiments, the insertion component 117 can be a second guide catheter 121. |
| 118 | Sheathed Balloon or Sheath Balloon | A balloon 111 that is naturally in an expanded state. The sheathed balloon 118 changes from a low-profile operating mode 132 into a high-profile operating mode 134 when it is removed from a sheath 119. The sheath 119 compresses a sheathed balloon 118 from what would otherwise be a high-profile operating mode 134 into a low-profile operating mode 132. In the some embodiments, the sheathed balloon 118 is a braid 124. |

TABLE 1-continued

| # | Name | Description |
|---|---|---|
| 119 | Sheath | A container of the sheathed balloon 118. The sheath 119 constrains the sheathed balloon 118 such that the sheathed balloon 118 remains in a low-profile operating mode 132 so long as the sheathed balloon 118 remains within the sheath 119. Upon removal from the sheath 119, the sheathed balloon 118 expands from a low-profile operating mode 132 into a high-profile operating mode 134. |
| 120 | Lumen | Space in the body of the patient 90 that is created by system 100. "Lumen" 120 is a medical term of art. The space is typically in the shape of a passageway or tunnel through the expansion component 110 for use by other medical devices 80 and/or in the performing of medical procedures 81 in the treatment of a patient 90. The transition of the expansion component 110 from a low-profile operating mode 132 into a high-profile operating mode 134 creates a lumen 120. |
| 121 | Guide Catheter | A tube through which other medical devices 80 or the expansion component 110 and other components of the system 100 can be inserted and positioned within the patient 90. Guide catheters 121 are a very common and fundamental medical device 80 used for vascular catheterization procedures. Different embodiments of the system 100 can involve zero, one, two, or even 3 or more guide catheters 121. |
| 122 | Guide Wire | A wire or similar cord used to "guide" other medical devices 80 to the desired location 88 within the patient 90. It can also be used to connect different components of the system 100 to each other. It is often useful to have a relatively thin wire 122 act in the lead of other components of the system 100. The guide wire 122 is a very common and fundamental medical device 80 used for vascular catheterization procedures. |
| 123 | Stent | A type of medical device 80 that can be implanted within the blood vessel 91 of a patient 90 to keep the vessel 91 open for blood flow. Some embodiments of the system 100 are intended to create a lumen to facilitate inserting the stent 123 to the desired location 88. The stent 123 can also be referred to as a stent catheter. |
| 124 | Braid or Braid Balloon | A type of self-expanding sheathed balloon 118 and a type of expansion component 110. The construction of the braid 124 can be designed to provide optimum performance. Braid 124 characteristics such as number of wires, shape of wire, wire material, pitch, uniform pitch, variable pitch and weave pattern can be chosen to obtain the desired performance. More or less wires, and wire material, can affect strength and flexibility of the component. Round wires or flat wires can affect wall thickness. Pitch and weave pattern can affect expansion strength and profile size. |
| 125 | Attachment Wire | A wire that is attached to a balloon 111 or other form of expansion component 110. Unlike a guide wire 122, the expansion component 110 does not move along the wire 125, but is fixed to the wire 125. |
| 126 | Medicinal Component | A substance used in diagnosing and/or treating a disease, illness, or medical condition in a patient 90. Some embodiments of the matrix 114 can include a medical component 126, typically in the form of a coating on the matrix 114. The matrix 114 may contain vaso-active agents to cause vasoconstriction or vasodilation, depending on what may be required. Such an agent may be transient or longer lasting. Nitric oxide is an example of a vaso-active agent that can dilate a vessel, which would make the vessel bigger (larger diameter) until the agent wears off. The matrix 114 may contain any of the class of drug coatings that prevent intimal hyperplasia. Intimal hyperplasia often is a physiologic response to an angioplasty procedure resulting in restenosis of the treated area, which in layman's terms is a clogged stent 123. |
| 130 | Operating Mode | A status or state of the expansion component 110. The expansion component 110 includes at least two operating modes 130: (a) a low-profile operating mode 132; and (b) a high-profile operating mode 134. Some embodiments of the system 100 may involve one or more operating modes 130 between the two extremes of a low-profile operating mode 132 and a high-profile operating mode 134. Many embodiments of the expansion component 110 can transform from a high-profile operating mode 134 back into a low-profile operating mode 132 when the lumen 120 is no longer required or desired. The operating mode 130 can also be referred to as a state 130. |
| 132 | Low-Profile Operating Mode | The operating mode 130 of the expansion component 110 in which the size of the space 120 is not maximized. Can also be referred to as a low-profile state 132. |

TABLE 1-continued

| # | Name | Description |
|---|------|-------------|
| 134 | High-Profile Operating Mode | The operating mode 130 of the expansion component 110 in which the size of the lumen 120 is maximized. Can also be referred to as a high-profile state 134. |
| 141 | Self-Expanding Helix Component | A helix balloon 113 that self-expands. In other words, the natural default state of a self-expanding helix component 141 is a high-profile operating mode 134 rather than a low-profile operating mode 132. |
| 142 | Mechanically-Expanding Helix Component | A helix balloon 113 that utilizes mechanical means such as springs to "inflate" (i.e. to transition between operating modes 130) rather than a gas or liquid. |
| 144 | Thread | A cord, fiber, wire, ribbon, strip or other strand of material used in a weave 145. |
| 145 | Weave | A weave 145 can be a configuration of one or more threads 144 that can contain the balloon 111 in the shape of a helix balloon 113. The weave 145 can use as many or as few threads 144 as desired. In many embodiments, between 10-12 threads 144 uniformly distributed about the helix balloon 113 is a particular desirable configuration. The weave 145 would wrap around the helix balloon 113 as the helix balloon 113 makes consecutive passes of the helical shape. |
| 146 | Bonding Agent | A chemical means to constrain the shape of the helix balloon 113. The matrix 114 can be made from a bonding agent 146 that is applied to a balloon 111 to secure its shape as a helix balloon 113. A bonding agent 146 can be used by itself or with other components to maintain the helical shape of the helix balloon 113. Consecutive passes of the helical shape can be bonded to adjacent passes. A wide variety of bonding agents including but not limited to adhesive glues or silicone can be used as possible bonding agents 146. The bonding agent 146 may be applied using dip coating techniques. |
| 147 | Thermally Formed Connection | A constraint on the helix balloon 113 that is implemented through the application of heat. A wide range of thermal forming techniques known in the prior art can be used to connect adjacent passes of the helical shape together. The aggregate configuration of thermally formed connections 147 can by itself or in conjunction with other components, constitute the matrix 114. |
| 148 | Matrix Cover | A relatively thin sheet or a collection of thin sheets that overlay the balloon 111 to shape it into a helix balloon 113. The matrix cover 148, which can also be referred to as a covering 148, can contain the helix balloon 113 and help maintain its helical shape. The matrix cover 148 can be made from a fabric or other similar material suitable for the particular location 88 in the patient 90. The matrix cover 148 can cover a single pass of the helical shape, multiple passes or all passes. The matrix cover148 can be used by itself or in conjunction with other components to constitute the matrix 114. The matrix 148 may be applied using dip coating techniques as well as other plausible manufacturing methods. |
| 149 | Flange | A flange is a rim, collar, or ring that secures the balloon 111 into the shape of a helix balloon 113. The cross-section of the helix balloon 113 can have one or more flanges 149. Adjacent passes of the helical shape can be connected together by the flange 149. The connected flanges 149 in the aggregate can form the matrix component 114. Flanges 149 can be connected using a weave 145, a bonding agent 146, a thermally formed connection 147, a matrix cover 148, and/or potentially other means. |
| 150 | Inflation Tube | A passageway to the balloon 111, such as a tubular balloon 112 or a helix balloon 113 that is used to inflate the balloon 111 with air or whatever gas or liquid is used to inflate the balloon 111. |
| 151 | Valve | The connection between the inflation tube 150 and the balloon 111. |

What is claimed is:

1. A method of performing angioplasty, the method comprising:
    accessing an artery; inserting a tubular balloon into to the artery in a low-profile operating mode, the tubular balloon constrained in a generally helical shape; situating the tubular balloon adjacent to a blockage in the artery; forming a lumen within the generally helical shape by expanding the tubular balloon into a high-profile operating mode in which an inner surface of the helical shape defines the lumen; passing a stent directly through the lumen such that there is no intervening structure between the inner surface of the helical shape and the stent; and implanting the stent into the blockage.

2. The method of claim 1, wherein the artery is accessed transradially.

3. The method of claim 1, wherein the artery is accessed transfemorally.

4. The method of claim 1, wherein the tubular balloon is expanded into the high-profile operating mode by inflating the tubular balloon.

5. The method of claim 1, wherein the tubular balloon is constrained in the generally helical shape by a matrix.

6. The method of claim 5, wherein in the matrix comprises a weave.

7. The method of claim 5, wherein the matrix comprises at least one thermally formed connection.

8. The method of claim 1, wherein the tubular balloon is inserted into the artery via an access point, and wherein the stent is provided to a working space defined by the lumen via the same access point.

9. A method of performing angioplasty, the method comprising:
   accessing an artery via an access point; inserting a tubular balloon into to the artery via the access point in a low-profile operating mode, the tubular balloon constrained in a generally helical shape; situating the tubular balloon adjacent to a blockage in the artery; forming a lumen within the generally helical shape by expanding the tubular balloon into a high-profile operating mode in which an inner surface of the helical shape defines the lumen; passing a stent through the lumen via the access point such that there is no intervening structure between the inner surface of the helical shape and the stent; and implanting the stent into the blockage.

10. The method of claim 9, wherein the artery is accessed transradially.

11. The method of claim 9, wherein the artery is accessed transfemorally.

12. The method of claim 9, wherein the tubular balloon is expanded into the high-profile operating mode by inflating the tubular balloon.

13. The method of claim 9, wherein the tubular balloon is constrained in the generally helical shape by a matrix.

14. The method of claim 13, wherein in the matrix comprises a weave.

15. The method of claim 13, wherein the matrix comprises at least one thermally formed connection.

16. The method of claim 9, wherein the lumen defines a working space, and the stent is passed directly through the working space, such that there is no intervening structure between the working space and the stent.

\* \* \* \* \*